(12) United States Patent
Andreu et al.

(10) Patent No.: US 7,768,151 B2
(45) Date of Patent: Aug. 3, 2010

(54) DEVICE FOR DISTRIBUTING POWER BETWEEN CATHODES OF A MULTIPOLAR ELECTRODE, IN PARTICULAR OF AN IMPLANT

(75) Inventors: David Andreu, Montpellier (FR); Serge Bernard, Saint-Georges d'Orques (FR); Yves Bertrand, Montpellier (FR); Guy Catheras, Grabels (FR); Jérôme Galy, Juvignac (FR); David Guiraud, Montpellier (FR); Jean-Denis Techer, Grabels (FR)

(73) Assignees: Inria Institut National de Recherche en Informatique et en Automatique, Le Chesnay Cedex (FR); Centre National de la Recherche Scientifique CNRS, Paris Cedex (FR); Universite de Montpellier II, Montpellier Cedex (FR)

( * ) Notice: Subject to any disclaimer, the term of this patent is extended or adjusted under 35 U.S.C. 154(b) by 632 days.

(21) Appl. No.: 11/661,360

(22) PCT Filed: Aug. 29, 2005

(86) PCT No.: PCT/FR2005/002161
§ 371 (c)(1),
(2), (4) Date: Apr. 5, 2007

(87) PCT Pub. No.: WO2006/027473
PCT Pub. Date: Mar. 16, 2006

(65) Prior Publication Data
US 2008/0061630 A1    Mar. 13, 2008

(30) Foreign Application Priority Data
Sep. 3, 2004    (FR) .................................. 04 09351

(51) Int. Cl.
H02M 1/00  (2007.01)
A61N 1/00  (2006.01)

(52) U.S. Cl. .......................................... 307/32; 607/62

(58) Field of Classification Search .................. 307/1, 307/31–33; 607/28, 2, 62, 39, 40, 42, 48, 607/123
See application file for complete search history.

(56) References Cited

U.S. PATENT DOCUMENTS

| | | | | |
|---|---|---|---|---|
| 5,190,035 A | * | 3/1993 | Salo et al. ...................... | 607/24 |
| 5,895,416 A | * | 4/1999 | Barreras et al. ................ | 607/62 |
| 5,954,758 A | | 9/1999 | Peckham et al. | |
| 6,144,881 A | * | 11/2000 | Hemming et al. ............. | 607/28 |
| 6,163,724 A | * | 12/2000 | Hemming et al. ............. | 607/28 |

FOREIGN PATENT DOCUMENTS

| | | |
|---|---|---|
| FR | 2 374 024 A | 7/1978 |
| FR | 2 587 624 A | 3/1987 |
| WO | WO 02/089913 A | 11/2002 |

* cited by examiner

Primary Examiner—Albert W Paladini
(74) Attorney, Agent, or Firm—Foley & Lardner LLP

(57) ABSTRACT

A device (ES) for distributing power between n cathodes (Ki) of at least one multipolar stimulating electrode (EM) comprises at least one anode (A), wherein n is equal to or greater than two. Said device (ES) comprises a reconfigurable current mirror (MC) which is provided with n outputs (K'i) connectable to said n cathodes (Ki), respectively and supplies to the n (K'i) outputs n complementary fractions of a control current having respective selected values which are substantially constant at the control current amplitude variation in order to carry out a substantially constant spatial location of stimulation.

39 Claims, 11 Drawing Sheets

Figure 1:
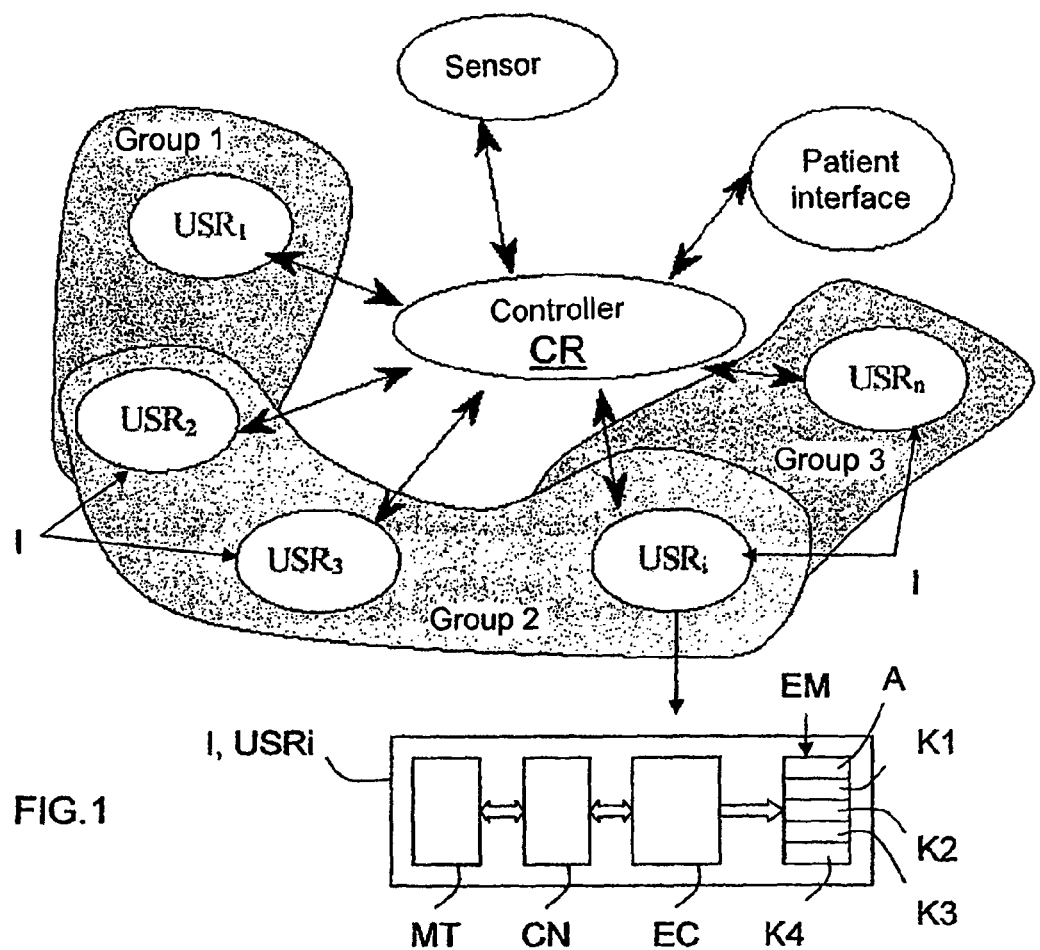

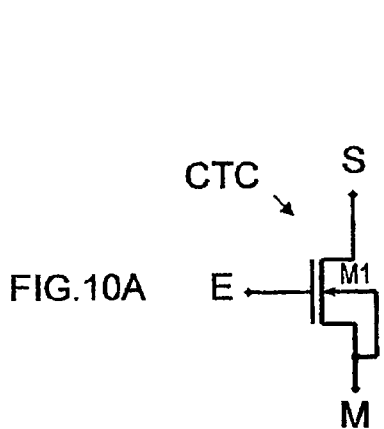
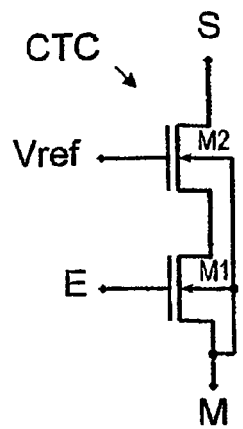
FIG.10A    FIG.10B
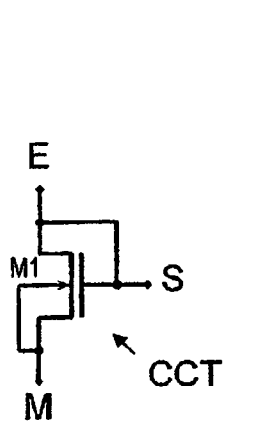
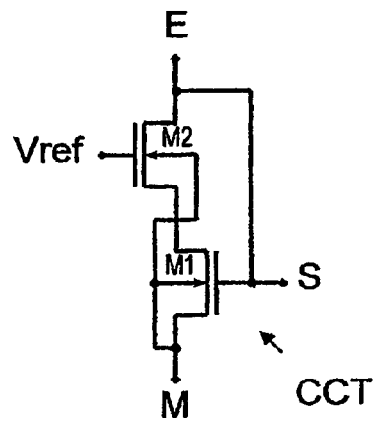
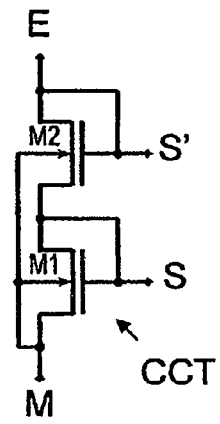
FIG.11A    FIG.11B    FIG.11C
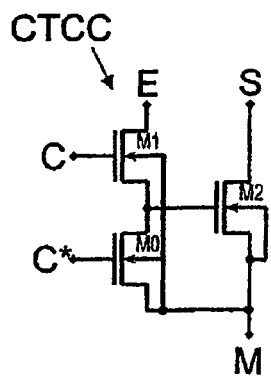
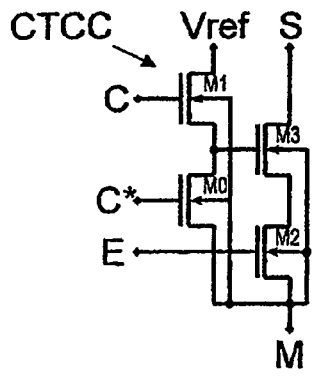
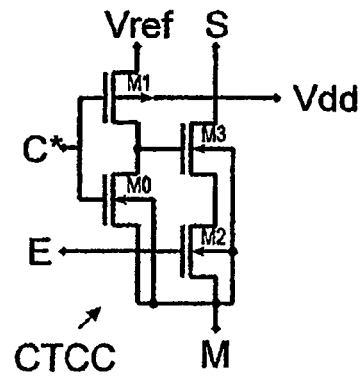
FIG.12A    FIG.12B    FIG.12C

DEVICE FOR DISTRIBUTING POWER BETWEEN CATHODES OF A MULTIPOLAR ELECTRODE, IN PARTICULAR OF AN IMPLANT

The invention relates to the field of the powering of multipolar electrodes, comprising at least one anode and at least two cathodes, and in particular those forming part of implants used for exciting or stimulating, for example, a zone of the brain, a smooth or striated muscle, an efferent or afferent nerve, a sensory organ, or more generally an element of the nervous system of a human or an animal.

In certain fields, it is essential to use multipolar electrodes in order effectively to excite one or more zones in accordance with a predefined model. This is, for example, the case in the field of functional electrical stimulation, which is currently the main method for restoring movement to paralyzed limbs: this stimulation is intended to activate one or more muscles by direct local excitation and/or by indirect excitation of a nerve using an electrical stimulus.

Currently, this type of stimulation is carried out using a central implant placed inside the body. Owing to the high degree of complexity of the means for managing a movement, various exciting electrodes have to be used, just as numerous wires are necessary for connecting the electrodes to the control electronics of the implants. As these wires frequently have to pass through joints, the surgical operations required for the implantation are particularly difficult, and this limits the number of excitation zones. Furthermore, the presence of wires weakens the implants and also limits the number of electrodes that they are able to control. Moreover, monitoring the form and the parameters, in particular time parameters, defining the electrical stimuli requires particular attention.

The object of the invention is therefore, in particular, to improve the situation.

The invention accordingly proposes, in particular, a device (or output stage) dedicated to distributing power between n cathodes of at least one multipolar stimulating electrode further comprising at least one anode, n being equal to or greater than two.

This device is characterised by the fact that it comprises a reconfigurable current mirror comprising n outputs coupled respectively to the n cathodes and configured to supply to these n outputs n complementary fractions of a control current having respective chosen values which are substantially constant in the presence of an amplitude variation of the control current so as to allow substantially constant spatial locating of the stimulation.

The term "complementary fractions" refers in the present context to fractions, the sum of which is equal to the value of the control current (Idac), such as for example Idac/3, Idac/6, Idac/6 and Idac/3.

The device according to the invention can comprise further characteristics capable of being taken separately or in combination, and in particular:

the reconfigurable multi-output current mirror can be of the modular type,
  it can then comprise a current/voltage converter coupled to p voltage/current converters with programmable transconductance,
  i) the current/voltage converter can comprise at least one input terminal responsible for absorbing a current, an earth terminal and an output terminal and be configured to establish a chosen potential difference between the output terminal and the earth terminal, as a function of the absorbed current,
  ii) each voltage/current converter with programmable transconductance can comprise at least one input terminal, an earth terminal, an output terminal responsible for absorbing a current and a control bus responsible for receiving logic signals,
  iii) the input terminal of the current/voltage converter is then connected to an input terminal of the modular reconfigurable multi-output current mirror,
  iv) the earth terminal of the current/voltage converter and the earth terminals of the p voltage/current converters with programmable transconductance are connected to the earth terminal M of the modular reconfigurable multi-output current mirror,
  v) the input terminal of each of the p voltage/current converters with programmable transconductance is connected to the output terminal of the current/voltage converter,
  vi) the output terminal of each of the p voltage/current converters with programmable transconductance is connected to one of the outputs of the modular reconfigurable multi-output current mirror, and
  vii) the control bus of each voltage/current converter with programmable transconductance is connected to control sub-buses of the modular reconfigurable multi-output current mirror,
the current/voltage converter and the p voltage/current converters with programmable transconductance preferably have matched architectures,
the reconfigurable multi-output current mirror can be of what is known as the "distributor" type,
  it can then comprise a current/voltage converter coupled to a voltage/current converter and to a controllable balanced current distributor having m outputs,
  i) the current/voltage converter can then comprise at least one input terminal responsible for absorbing a current, an earth terminal and an output terminal, and be configured to establish a chosen potential difference between the output terminal and the earth terminal, as a function of the absorbed current,
  ii) the voltage/current converter can comprise at least one input terminal, an earth terminal and an output terminal capable of absorbing a current,
  iii) the controllable balanced current distributor can comprise at least one input terminal responsible for supplying a current, a bus of outputs, each absorbing a current, and a control bus receiving logic signals,
  iv) the input terminal of the current/voltage converter is then connected to an input terminal of the distributor-type reconfigurable multi-output current mirror,
  v) the earth terminal of the current/voltage converter and the earth terminals of the voltage/current converter and the controllable balanced current distributor are connected to an earth terminal of the distributor-type reconfigurable multi-output current mirror,
  vi) the input terminal of the controllable balanced current distributor is connected to the output terminal of the voltage/current converter,
  vii) the control bus of the controllable balanced current distributor is connected to a control bus of the distributor-type reconfigurable multi-output current mirror, and viii) the output bus of the controllable balanced current distributor is connected to an output bus of the distributor-type reconfigurable multi-output current mirror, the current/voltage converter and the voltage/current converter preferably have matched architectures, the ratio between the current circulating in the anode (equal to the sum of the currents supplied to the outputs of the current mirror) and the control current can be configurable or non-configurable, a set of n capacitors can each couple one of the outputs to one of the cathodes, a voltage monitoring device can be connected to the outputs and responsible for measuring the voltages respectively present at the outputs of the current mirror, so they allow adjustment of the anode polarization of the multipolar electrode via a high-voltage supply module, it can comprise a network of analogue/digital converters or else a network of n voltage comparators, each responsible for comparing the n voltages at the outputs of the current mirror relative to a common reference voltage, or else a network of 2n voltage comparators configured in pairs to compare the n voltages at the outputs of the current mirror relative to common reference voltages, a discharge control device can be coupled to the outputs of the current mirror and to the anode and be responsible for establishing, at the end of the stimulation, a conduction path between each of the outputs of the current mirror and the anode, so as to induce the circulation of n discharge currents from the cathodes to the anode, these n discharge currents can originate from the n energies respectively stored by the n capacitors of the set, it can be responsible for limiting each discharge current to a fraction of the maximum value of the stimulation current supplied to the associated output.

A current distribution device of this type (or output stage) can advantageously form part of control electronics of at least one multipolar electrode, comprising at least one anode and at least two cathodes. These control electronics then further comprise i) a digital/analogue converter responsible for converting a current amplitude reference value into a control analogue current and coupled to the current distribution device to provide it with the control current, and ii) a high-voltage supply module coupled at least to the anode and responsible for polarizing the anode under a chosen voltage, so it allows circulation of the currents imposed on each cathode via the current distribution device.

The digital/analogue converter can have what is known as a "unit current source" architecture, ensuring the monotonicity of its conversion function.

The high-voltage supply module can be a "DC/DC"-type converter. In this case, it can be configured in the form of an inductive storage chopper (for example of the "boost" type) or else comprise a capacitive storage charge pump, such as for example a Dickson pump, optionally coupled to a multiplexer. In this last case, the high-voltage supply module can operate either continuously or discontinuously.

The invention also relates to a distributed stimulation unit (USR), such as for example an implant, comprising at least one multipolar electrode, comprising at least one anode and at least two cathodes, and at least one control electronics of the type of that presented hereinbefore.

This distributed stimulation unit can comprise a digital controller (CN) responsible for supplying the current amplitude reference value and for defining the values of the current fractions supplied to the outputs of the reconfigurable multi-output current mirror. In this case, the digital controller and the control electronics (EC) can, for example, respectively form a digital part and an analogue part of a mixed-type ASIC.

Furthermore, the digital controller can be responsible for deducing, from the values of the imposed stimulation currents, from the output voltage of the high-voltage supply module and from the voltage measurements carried out by the voltage monitoring device at the output terminals of the reconfigurable multi-output current mirror, the impedance of each electrode, so as to control the polarization of the anode.

The invention also relates to a stimulation system comprising at least one distributed stimulation unit of the type of that presented hereinbefore and a controller (CR) responsible for exchanging data with each distributed stimulation unit.

Moreover, each distributed stimulation unit and the controller of the system can comprise wave (or wired bus) transmission means and management means responsible for managing the data transmission in accordance with a protocol chosen between said controller and each distributed stimulation unit.

The invention also relates to a protocol for communication between a controller of a system of the type of that presented hereinbefore and at least one distributed stimulation unit of the type of that presented hereinbefore, via a medium. This protocol is characterised by the fact that it consists in managing access to the medium in accordance with a principle of the right to speak of group(s) of distributed stimulation units at sliding intervals, based on an automatic positioning of time intervals which is dependent on levels of priority respectively associated with each node within its group and on topological characteristics, such as for example the data rate and the propagation time.

This means for managing access to the medium is, for example, intended to optimize the exploitation of the bandwidth.

The current distribution device (or output stage), the control electronics, the distributed stimulation unit (implant), the stimulation system and the communication protocol presented hereinbefore are particularly well adapted to the stimulation of animal or human nerve(s) and/or muscle(s).

Figure 2:
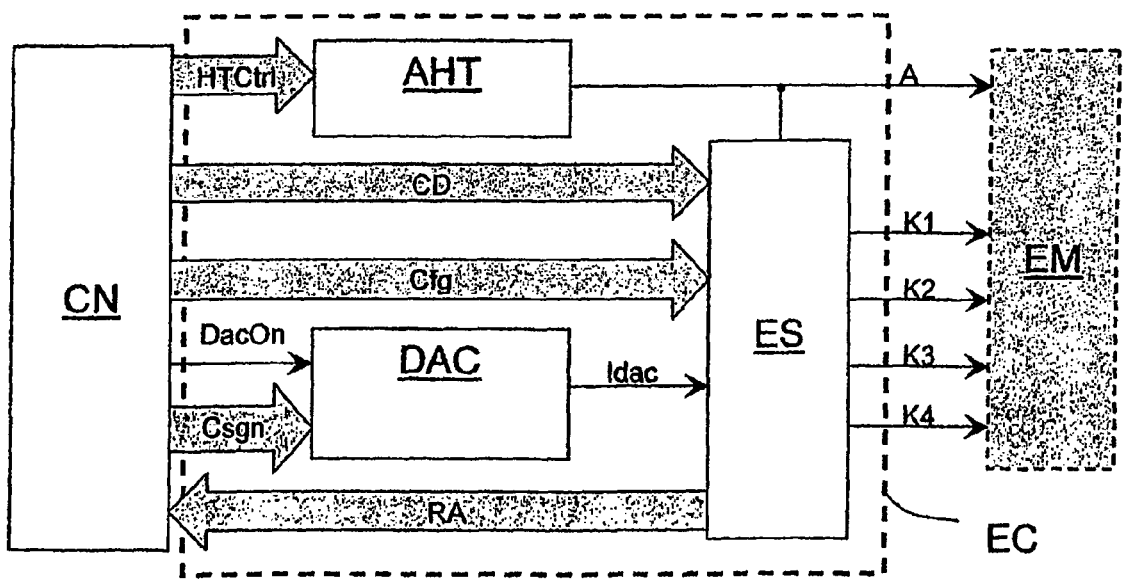
Figure 3:
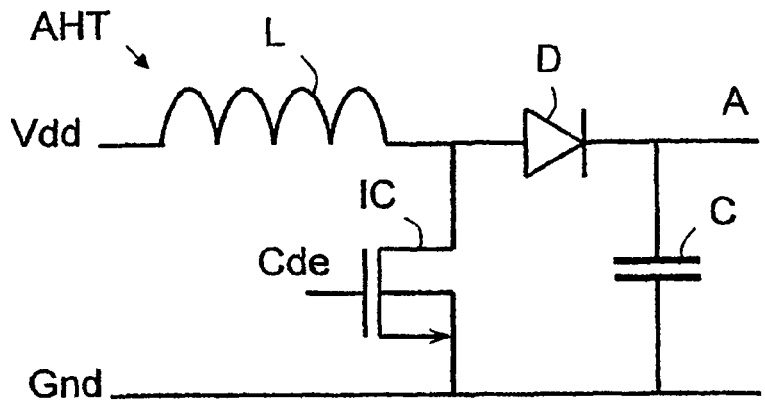
Figure 4:
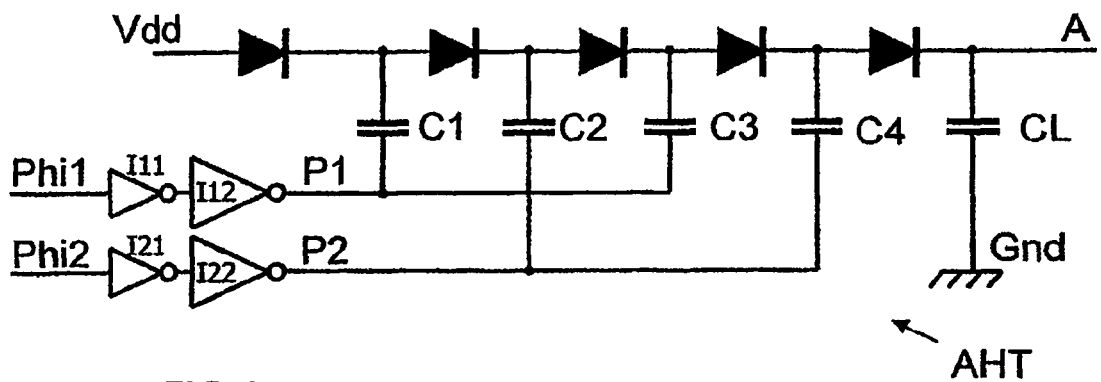
Figure 5:
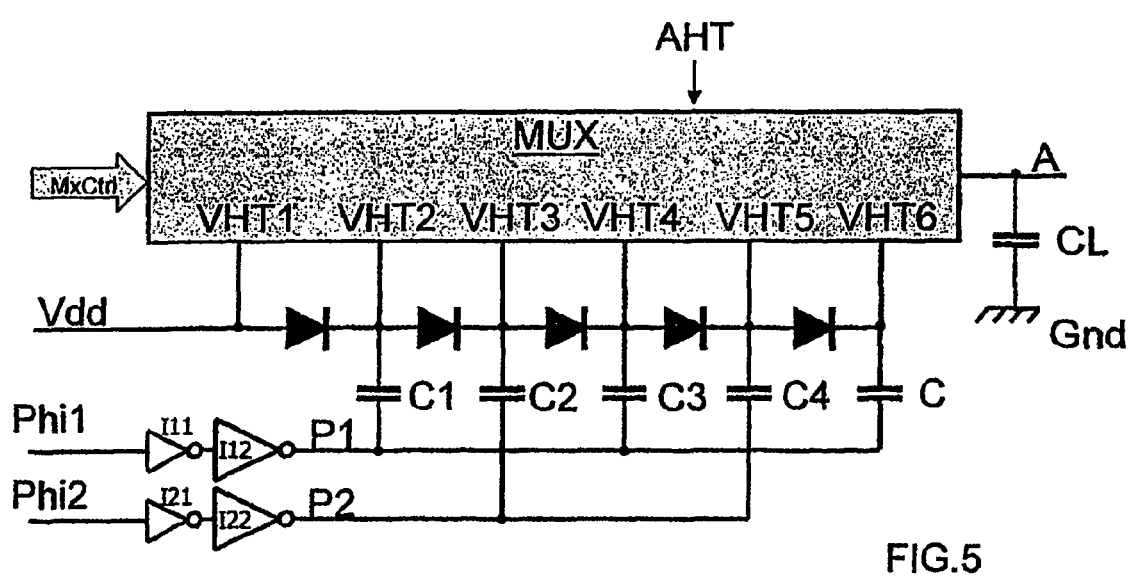
Figure 6:
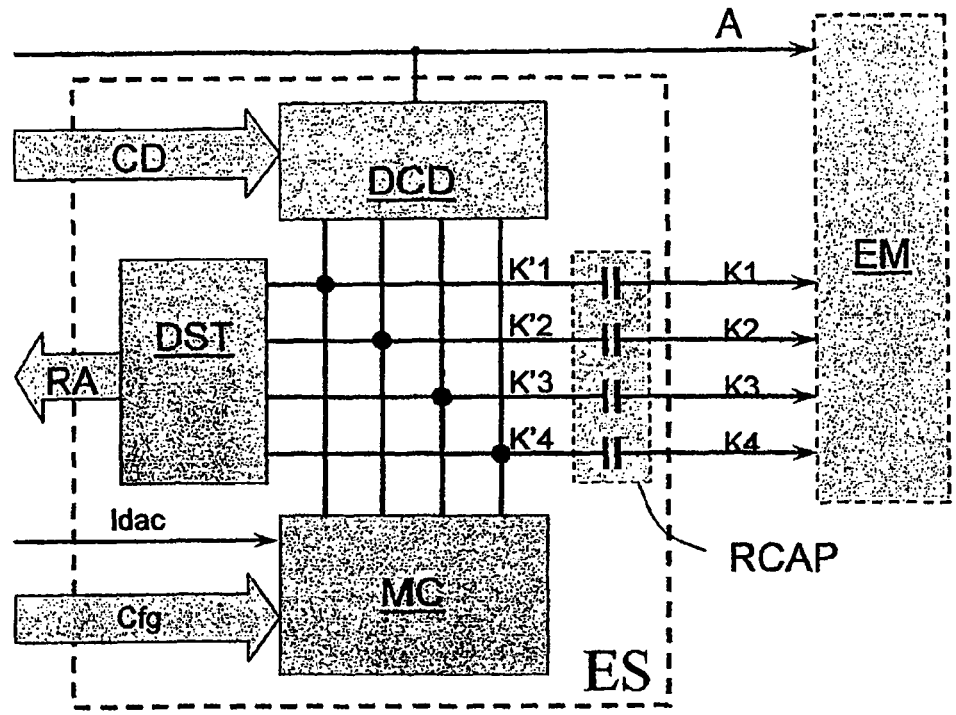
Figure 7:
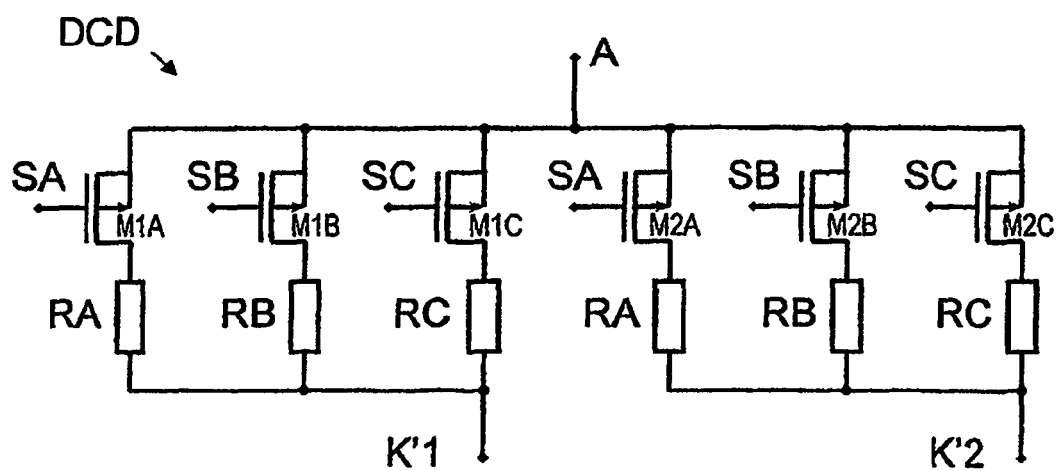
Figure 8:
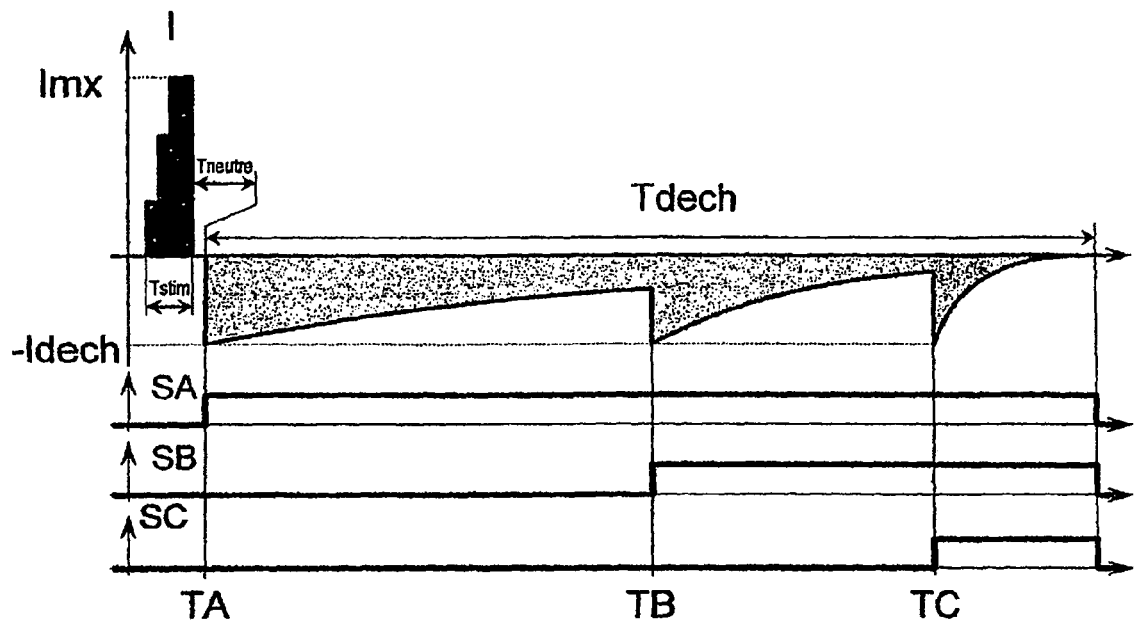
Figure 9:
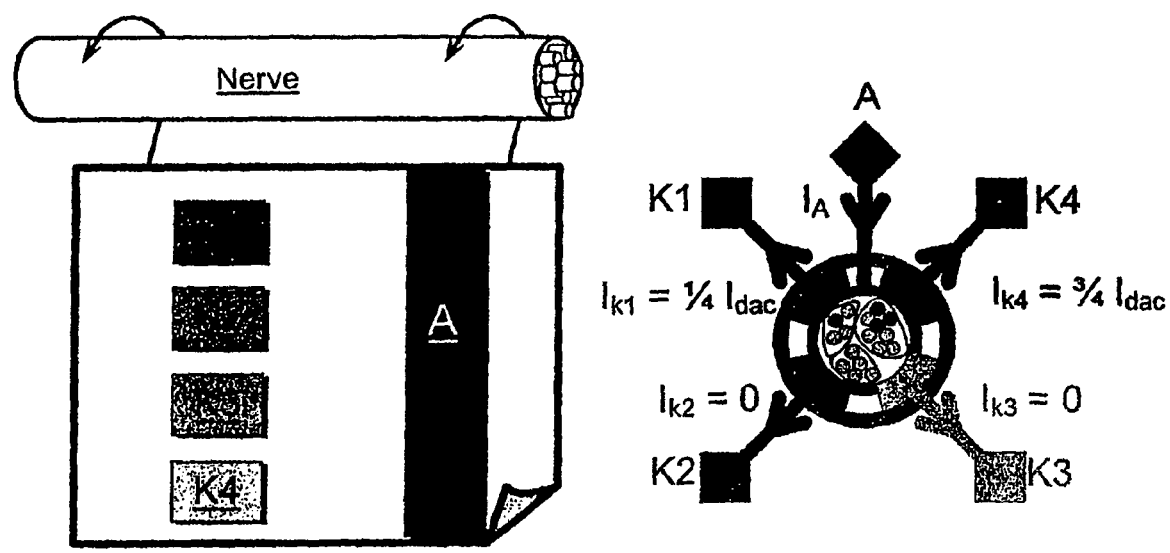
Figure 13:
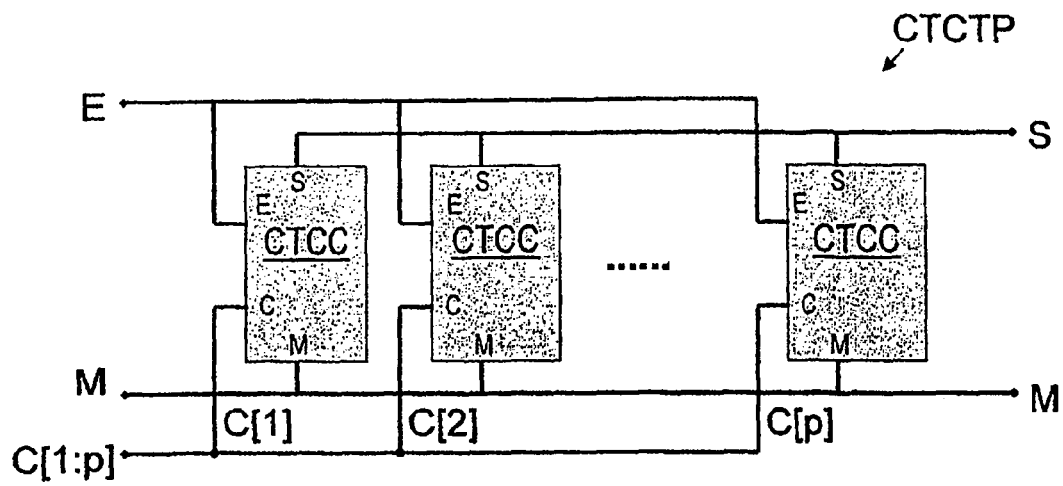
Figure 14:
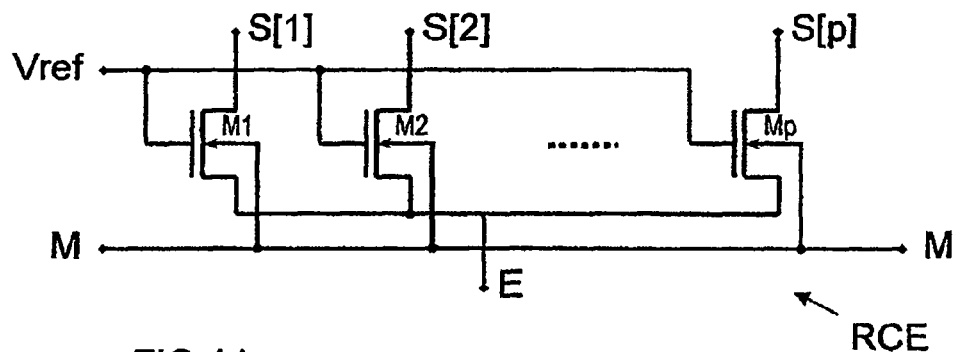
Figure 15A:
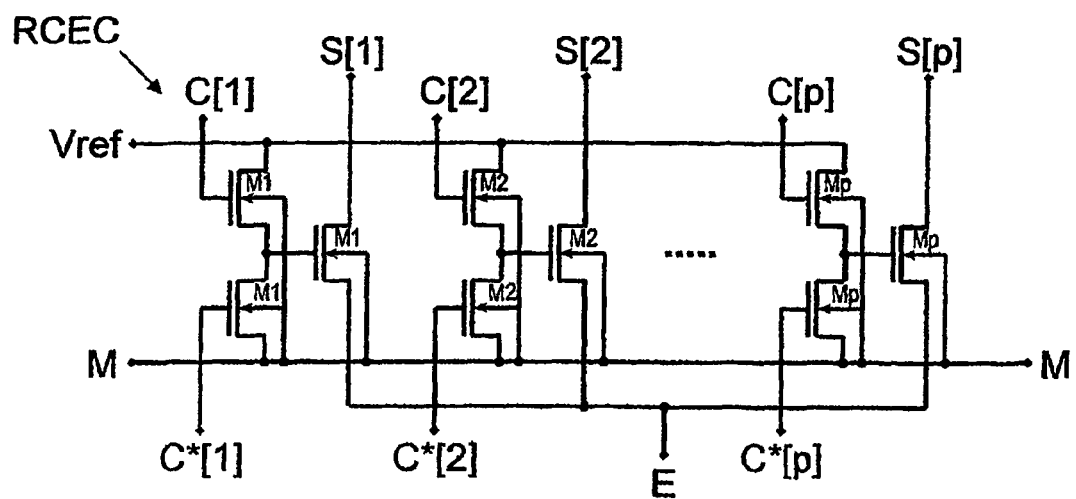
Figure 15B:
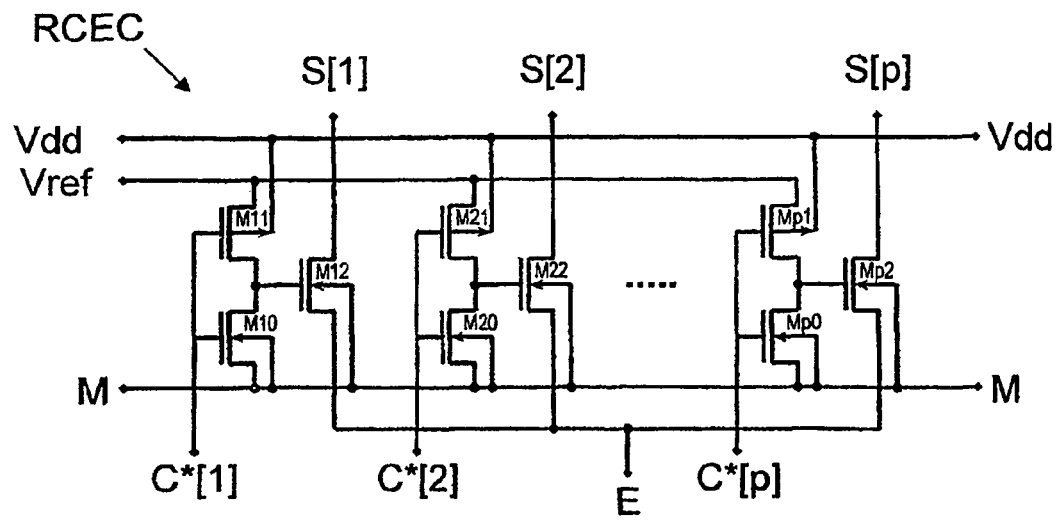
Figure 16:
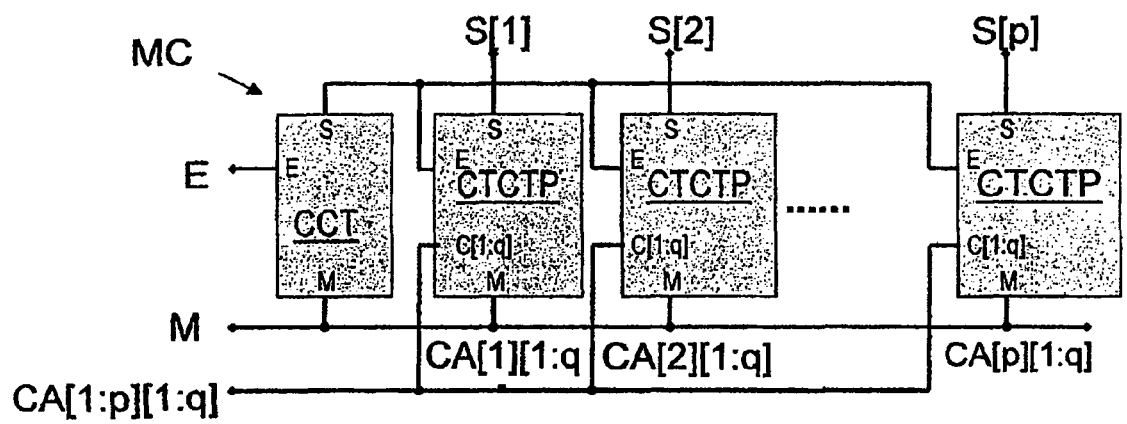
Figure 17:
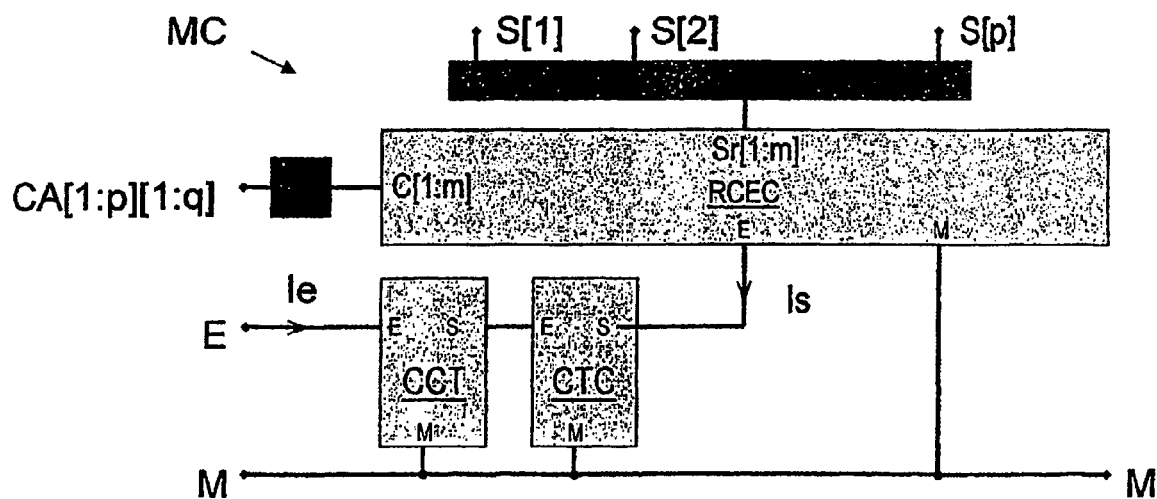
Figure 18:
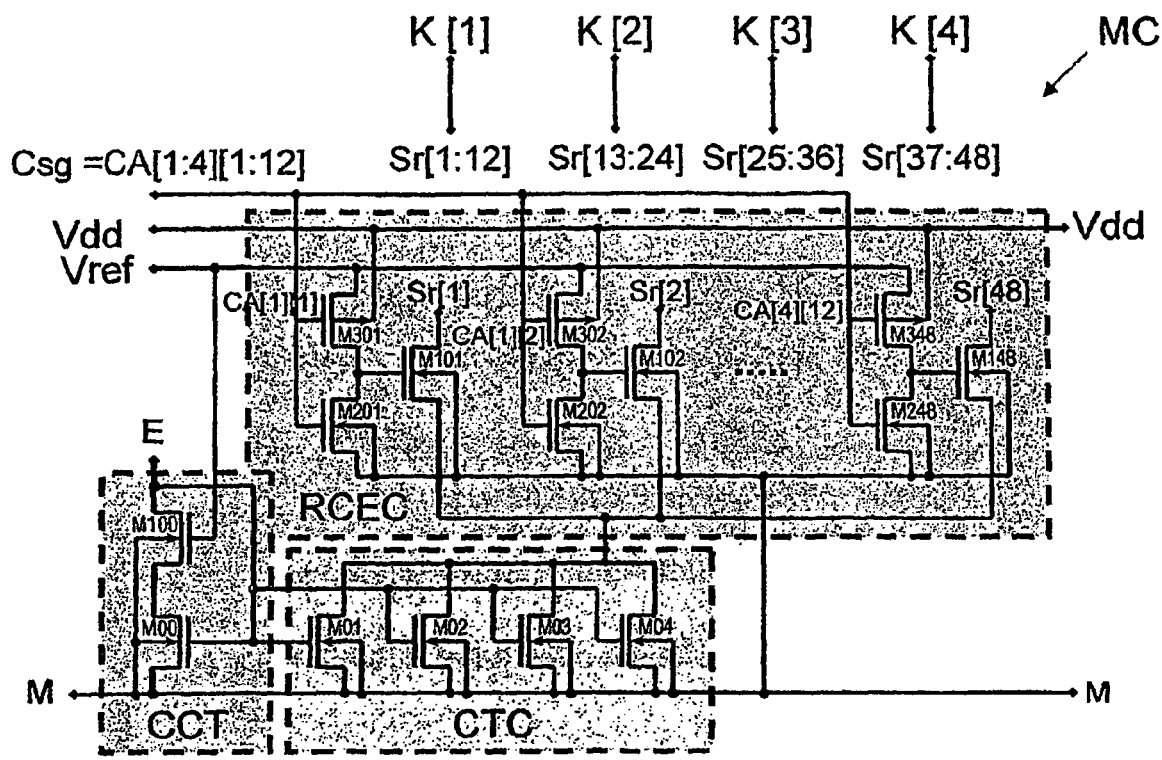
Figure 19:
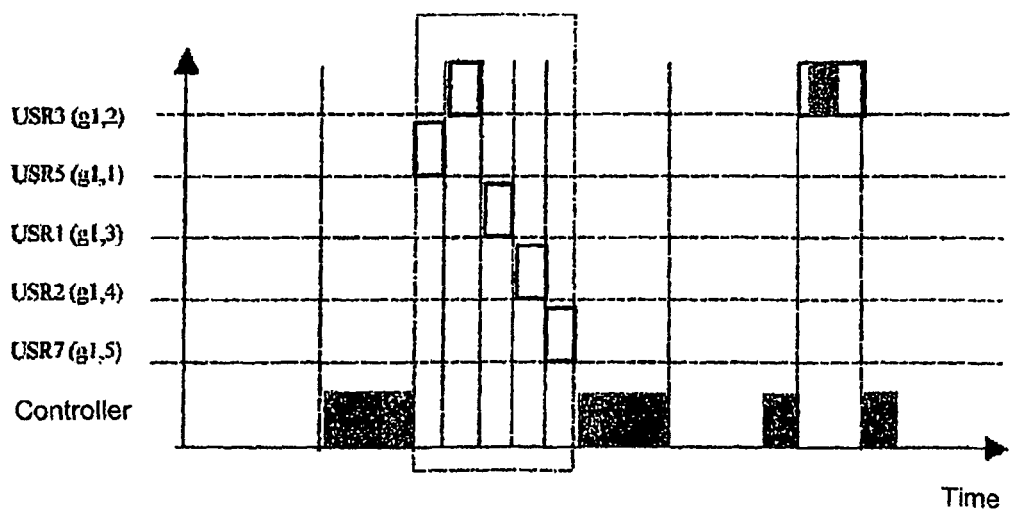
Figure 20:
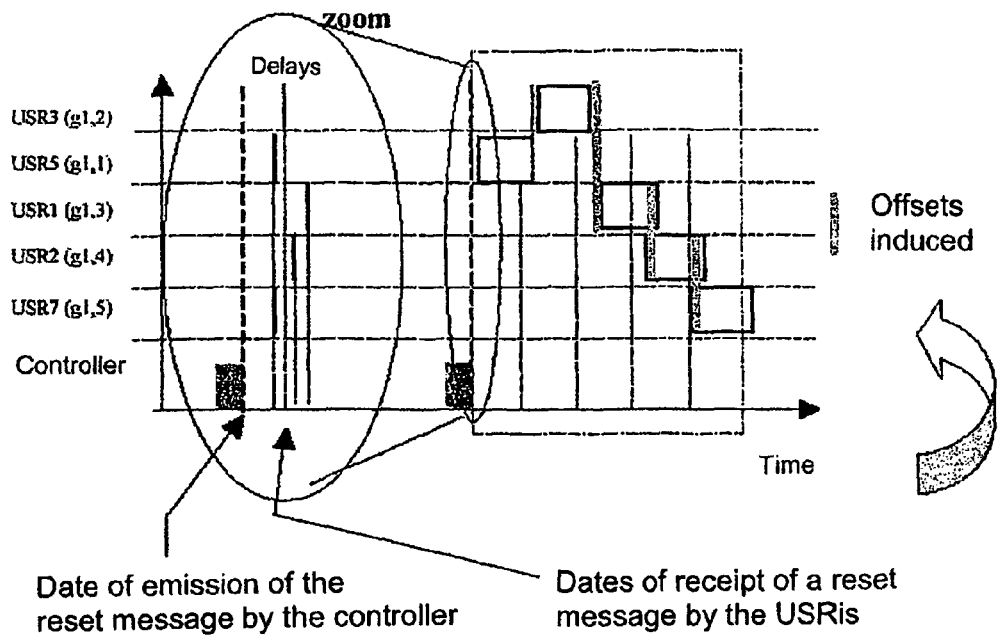
Figure 21:
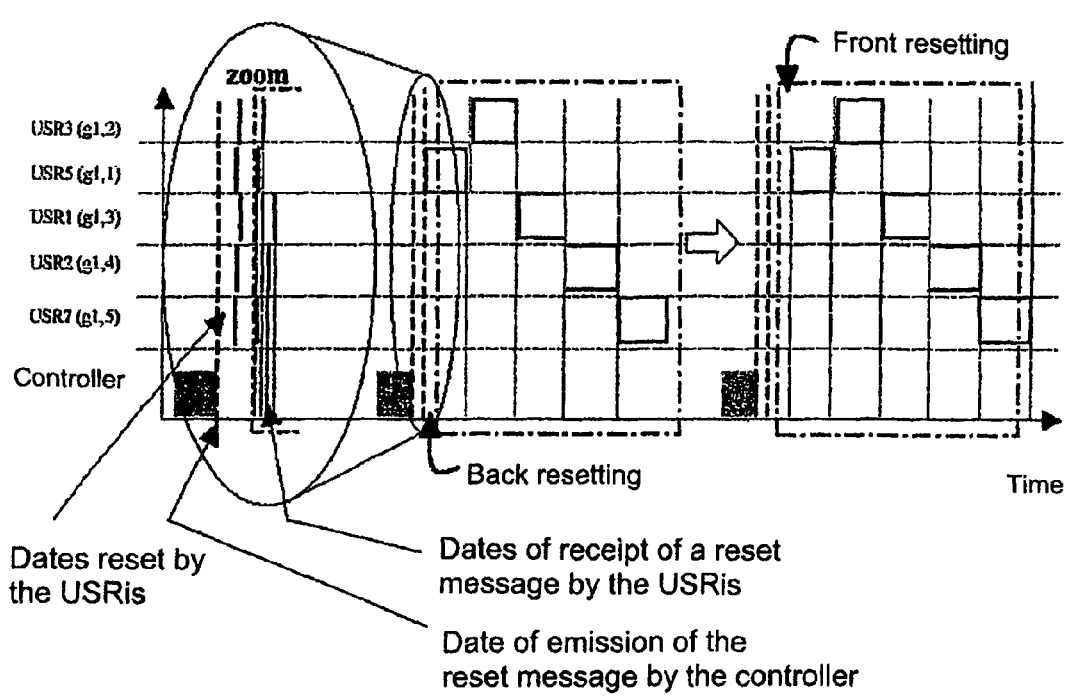
Figure 22:
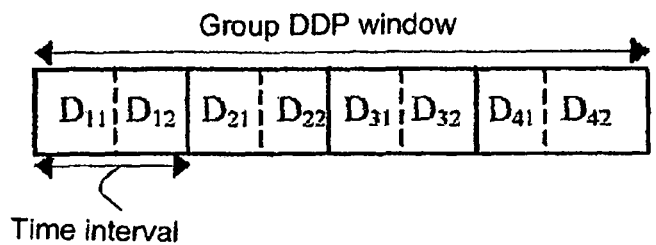
Figure 23:
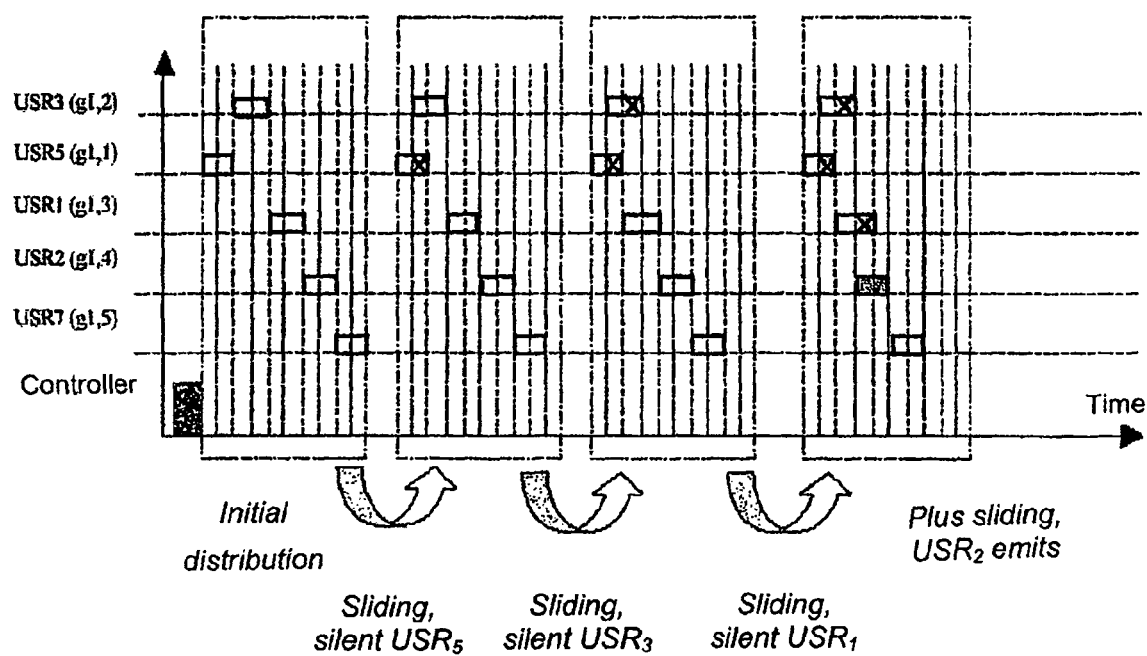
Figure 24:
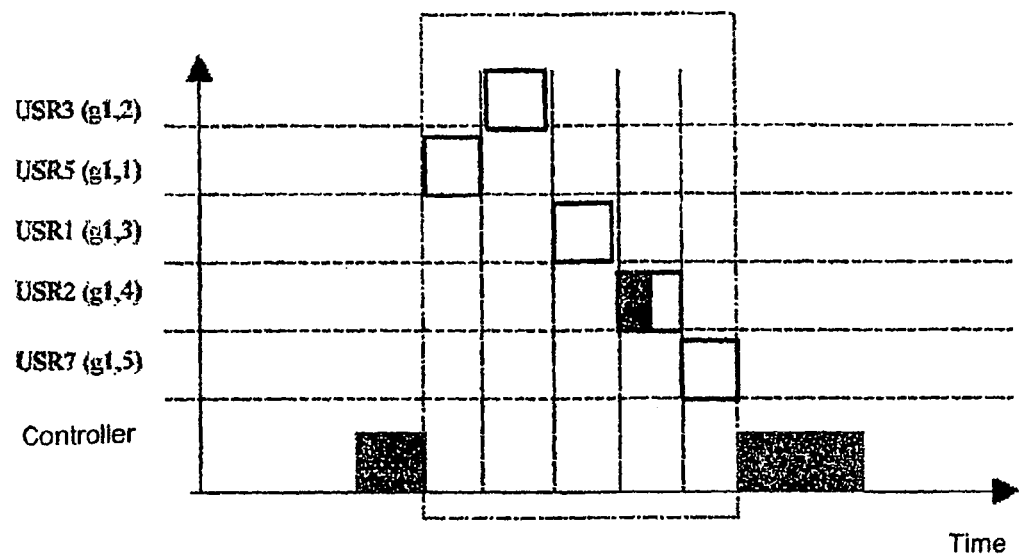
Figure 25:
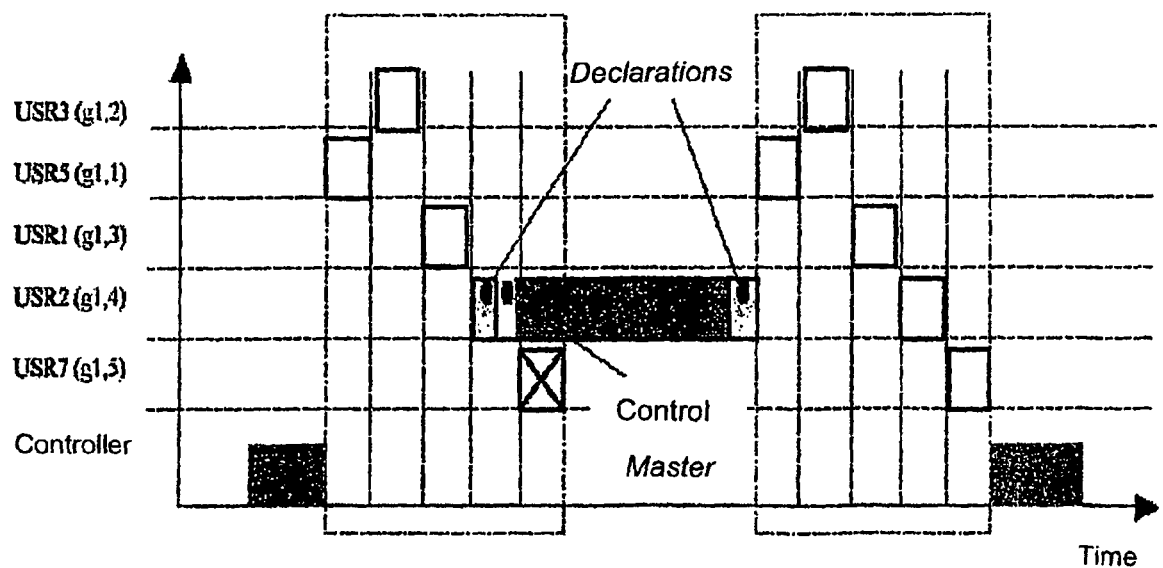

Further characteristics and advantages of the invention will become apparent on examining the following detailed description and the appended drawings, in which:

FIG. 1 illustrates highly schematically an example of a stimulation system according to the invention, FIG. 2 illustrates schematically an example of control electronics according to the invention coupled to a multipolar electrode and to a digital controller, FIG. 3 illustrates schematically a first example of a "boost"-type chopper high-voltage supply module for control electronics according to the invention, FIG. 4 illustrates schematically a second example of a Dickson pump high-voltage supply module for control electronics according to the invention, FIG. 5 illustrates schematically a third example of a Dickson pump and multiplexer high-voltage supply module for control electronics according to the invention, FIG. 6 illustrates schematically an example of an output stage for control electronics according to the invention, FIG. 7 illustrates schematically an example of a discharge control module for an output stage of control electronics according to the invention, FIG. 8 illustrates examples of time charts defining the time characteristics of the current I passing through the multipolar electrode and of control signals (SA, SB and SC) of the discharge control module, originating from the digital controller, FIG. 9 illustrates schematically an example of a multipolar electrode before being wound around a nerve (left-hand portion) and a cross section of an example of a nerve and the nerve fibres thereof equipped with said multipolar electrode (right-hand portion) in the case of a (¼, 0, 0, ¾)-type current distribution, FIGS. 10A and 10B illustrate schematically two embodiments of a current/voltage converter for a reconfigurable multi-output current mirror of an output stage of control electronics according to the invention, FIGS. 11A to 11C illustrate schematically three embodiments of a voltage/current converter for a reconfigurable multi-output current mirror of an output stage of control electronics according to the invention, FIGS. 12A to 12C illustrate schematically three embodiments of a controllable voltage/current converter for a reconfigurable multi-output current mirror of an output stage of control electronics according to the invention, FIG. 13 illustrates schematically an embodiment of a voltage/current converter with programmable transconductance for a reconfigurable multi-output current mirror of an output stage of control electronics according to the invention, FIG. 14 illustrates schematically an embodiment of a balanced current distributor for a reconfigurable multi-output current mirror of an output stage of control electronics according to the invention, FIGS. 15A and 15B illustrate schematically two embodiments of a controllable balanced current distributor, with N channel FETs and with N channel and P channel FETs respectively, for a reconfigurable multi-output current mirror of an output stage of control electronics according to the invention, FIG. 16 illustrates schematically an embodiment of a modular-type reconfigurable multi-output current mirror for an output stage of control electronics according to the invention, FIG. 17 illustrates schematically an embodiment of a "distributor"-type reconfigurable multi-output current mirror for an output stage of control electronics according to the invention, FIG. 18 illustrates in greater detail a further embodiment of a "distributor"-type reconfigurable multi-output current mirror for an output stage of control electronics according to the invention, FIG. 19 illustrates schematically the notions of the individual right to speak and the group right to speak within a stimulation system according to the invention, FIG. 20 illustrates schematically the offsetting induced by relative positioning, FIG. 21 illustrates schematically the resetting in the case of relative positioning, FIG. 22 illustrates schematically a time window associated with a group of USRs and the breaking-down thereof into time intervals associated with each of the USRs of said group, FIG. 23 illustrates schematically the time interval sliding mechanism within a group of USRs, FIG. 24 illustrates schematically a first example of a time chart of access to the medium, and FIG. 25 illustrates schematically a second example of a time chart of access to the medium.

The appended drawings may serve not only to supplement the invention but also, if appropriate, to contribute to the definition thereof.

The invention is intended to allow distributed powering of the cathodes of at least one multipolar electrode.

It will be assumed hereinafter, by way of non-limiting example, that the electrode forms part of an implant intended to be implanted into a human or animal body in order to stimulate one or more zones such as, for example, one or more nerves and/or one or more muscles. However, an electrode of this type could be used in further fields such as, for example, stimulation of the brain or stimulation of the sensory systems at the afferent pathways or biological sensors themselves.

As is schematically illustrated in FIG. 1, an implant I (or USR, distributed stimulation unit) basically consists of a digital controller CN coupled, on the one hand, to transmission means MT and, on the other hand, to control electronics EC, themselves coupled to a multipolar electrode EM comprising at least one anode A and at least two cathodes Ki (i=1 to 2). If the multipolar electrode EM is dedicated to the stimulation of a nerve, it is advantageous for it to be configured in the form of a cylinder and comprise at least one anode A and, for example, four cathodes K1 to K4 (i=1 to 4). However, other forms of electrodes are conceivable.

As illustrated in FIG. 1, the implant can, in association with one or more other implants, form part of a stimulation system IS. In this case, each implant I forms what is known as a distributed stimulation unit (USR) and the installation preferably comprises an external controller (CR) coupled to each implant I, preferably by way of waves (for example of the radiofrequency RF type), but coupling by wired bus is also conceivable. This coupling is intended to allow the exchange of data between each implant I and the controller CR of the system IS. The controller CR can thus transmit to each implant I data, defining for example configuration or interrogation messages, and optionally power. Moreover, an implant I can transmit to the controller CR data defining, for example, stimulation error or incoherent order notifications or acknowledgements.

Such transmission can, for example, be carried out in asynchronous packet mode. Furthermore, the transmission, at least from the controller CR to the implants I, can be carried out in point-to-multipoint (or multicast) broadcast mode if it relates to a group of implants of the system, or in general broadcast mode if it relates to all the implants of the system, or in point-to-point (or unicast) mode if it relates merely to a single implant of the system.

The stimulation system can also comprise one or more sensors coupled to the controller CR and/or a patient interface also coupled to the controller CR and allowing the patient, the subject of the stimulation, to interrupt a stimulation programme, for example.

Moreover, as will be seen hereinafter, the implants I (or USRs) can be dynamically grouped into various groups allowing, for example, simultaneous control of a minimum group of implants I (or USR) required to obtain a given movement and certain implants (or USRs) which can belong to differing groups (as is the case in the present instance for USR2 and USRi).

For example, raising of a foot requires simultaneous contraction of the three flexors of the hip, the knee and the ankle; the three USRs stimulating these muscles can therefore be grouped for this movement.

Reference will now be made to FIG. 2 to present the main components of the control electronics EC of an implant I according to the invention. It is important to note that the control electronics EC illustrated in FIG. 2 are dedicated to a multipolar electrode EM comprising four cathodes Ki (i=1 to 4). However, the invention is not limited to this type of multipolar electrode. It relates to any stimulation device having at least one anode and at least two cathodes.

In order to facilitate understanding of the description, a plurality of definitions are provided hereinafter:

an ASIC is in the present context an application-specific integrated circuit, a mixed ASIC is in the present context an ASIC comprising digital processing parts and analogue processing parts, Vdd denotes the positive terminal for the electrical powering of an implant I and, equally, the value of the supply voltage. This value is, for example, equal to 3 volts (V), although any other voltage, for example one better adapted to the embodiment of the ASIC, can be used, Gnd denotes earth and, equally (as they are connected), the negative terminal for the electrical powering of an implant I or earth or the substrate of the ASIC if the technology of the ASIC necessitates connecting the substrate thereof to the lowest potential, as is the case in CMOS technology on a P-type substrate.

Moreover, within a bus, all the signals carry the name of the bus and distinguished by an index placed in square brackets after the name of the bus. Furthermore, if the size of the bus has to be specified, the name of the bus is followed by a pair of square brackets containing the lowest index and the highest index of the wires forming the bus, separated by the character ":". The same notation can be used to refer to a portion of a bus. Finally, for particularly complex buses, a multidimensional notation can be used. Certain examples of notations are provided hereinafter:

X denotes both a signal and a bus,

X[1:10] denotes a bus having ten signals,

X[3] denotes the third signal from the bus referred to as X,

X[3:5] denotes a bus formed by the extraction of three signals from the bus X,

Y[1:5][1:4] denotes a bus having 20 (5×4) signals, organized into five sub-buses, each having four signals, Y[3][2] represents a signal, and Y[3] is a bus having four signals which can also be written as follows: Y[3][1:4].

The control electronics can, for example, be in the form of an analogue part of a mixed ASIC, the digital part of which can comprise a digital controller CN, of the type of that shown in FIG. 2, which will be described hereinafter merely in terms of the commands that it is liable to send to the control electronics EC. The transmission means MT illustrated in FIG. 1 will not be described in the present case either.

The control electronics EC comprise at least three parts.

A first part consists of a digital/analogue converter DAC responsible for converting a current amplitude reference value (Csgn) received by the digital controller CN into an output analogue current Idac.

A second part consists of a high-voltage supply module AHT responsible for polarizing the anode A of the multipolar electrode EM under a sufficiently high voltage to allow circulation of the current imposed on each cathode by the output stage ES (also referred to as the current distribution device). This high voltage can, for example, be generated from the low-voltage supply Vdd.

A third part consists of the output stage ES (also referred to as the current distribution device) which is intended mainly to distribute the output analogue current Idac into fractions and to transmit them to the various cathodes Ki of the multipolar electrode EM. As will be seen hereinafter, this output stage ES also preferably compensates for the charges stored by the current passing through the multipolar electrode EM in order to ensure that the average value of the stimulation current passing through each cathode Ki is zero.

The three parts of the control electronics EC receive the electrical power supply Vdd and earth Gnd.

The converter DAC is, for example, an eight-bit digital/analogue converter operating in current mode. The current can, for example, be programmed to range from 0 to 1.25 mA, optionally by increments of 5 µA. This converter DAC preferably uses what is known as a "unit current source" architecture which ensures the monotonicity of its conversion function.

Moreover, the converter DAC has an input DacOn which forces it, when it is placed at logic level "0", to supply a zero current (Idac=0) and which allows it, when it is placed at logic level "1", to validate an output current Idac equal to $(2^N-1)$*I_LSB. In this case, N represents the number of bits of the converter (for example, N=8 bits) and I_LSB represents the quantification increment of the converter (for example, 5 µA).

In order to minimize overall consumption, use can optionally be made of a converter DAC which minimizes, or even eliminates, its power consumption when its input DacOn is placed to logic level "0".

The high-voltage supply module AHT provides the anode polarization voltage from the multipolar electrode EM. For most of the stimulations, this voltage is higher than the supply voltage Vdd. The high-voltage supply module AHT is therefore preferably a "DC/DC"-type converter. In order to limit the amount of power consumed, the anode polarization voltage can be fixed beforehand by the digital controller CN based on the stimulation current to be applied. Moreover, the output stage ES sends to the digital controller CN an item of information RA relating to the amplitude of the voltage at the terminals of the current generators controlling the various cathodes Ki. This item of information RA can then be used during the stimulation phase to adjust the anode polarization.

This high-voltage supply module ART can, for example, be in the form of an inductive storage chopper (for example, of the "boost" type). As a person skilled in the art is aware, a chopper of this type is controlled by a single control signal, the frequency and cyclic ratio of which determine the output voltage for a given charge. FIG. 3 illustrates an example of a boost-type chopper using four components: an inductor L, a capacitor C, a diode (for example of the "Schottky" type having a low threshold voltage) D and a controlled switch IC. In this embodiment, the input signal Cde forms in itself the cluster denoted by HTCtrl in FIG. 2.

The components L, D and C are preferably discrete components outside the ASIC. Furthermore, the controlled switch IC can be either a discrete, optionally specialized, component, or a device integrated into the ASIC such as, for example, a field effect transistor with an insulated gate and an N channel, as illustrated in FIG. 3.

In one variation, the high-voltage supply module AHT can comprise a capacitive storage charge pump such as, for example, a Dickson pump using CMOS technology. FIG. 4 shows an example of a Dickson pump with five stages. In this case, the diodes are generally produced with MOS transistors, for example N channel transistors, the gate of which is connected to the drain. Use can thus be made of more complex models allowing the threshold voltage to be dispensed with. In this figure, FIG. 4, reference numerals I11, I12, I21 and I22 denote CMOS inverters powered between Vdd and Gnd and appropriately designed so as to allow the capacitors to be charged within a time compatible with the envisaged operating frequency. If the signals P1 and P2 are two rectangular signals having the same frequency, the output voltage under the pump vacuum depends merely on the number of stages and on the value of Vdd. Moreover, the operating frequency controls the output resistance of the converter, thus providing a means for controlling the charged output voltage. The number of stages is accordingly imposed by the maximum voltage to be provided at point A and the cluster HTCtrl in FIG. 2 consists merely of the input signals Phi1 and Phi2.

In a further variation, illustrated in FIG. 5, the high-voltage supply module AHT comprises a Dickson pump associated with an analogue multiplexer MUX. In a Dickson pump, the voltages available on each stage differ from Vdd, so the multiplexer MUX provides a full range of voltages allowing the anode polarization voltage to be adjusted. In this embodiment, the multiplexer MUX allows the circulation of a current from one of its inputs VHTi (in this case i=1 to 6), chosen by the digital controller CN, to the output A, the circulation of a current from A to one of the inputs VHTi being prohibited. In this way, the digital controller CD can adapt the anode voltage, by increment of Vdd, without having to vary the operating frequency. The cluster MxCtrl comprises as many wires as the multiplexer has inputs VHTi. If a high-voltage supply module AHT of this type is used, the cluster HTCtrl in FIG. 2 is composed of the cluster MxCtrl associated with the signals Phi1 and Phi2.

This multiplexer MUX can, for example, be in the form of a star, of which the output A is the centre and of which the inputs VHTi are the ends of the arms. Each arm of the star can then contain a controlled rectifier (for example, a diode in series with an insulated gate field effect transistor (FET)). The gate of said transistors is then controlled by the logic signals of the cluster MxCtrl via logic-level adapters, optionally powered by an additional stage of the charge pump (not shown here).

This other variation of the high-voltage supply module AHT can be used either continuously or discontinuously. In continuous mode, the pump is actuated during the stimulation (rectangular signals in phase opposition to Phi1 and Phi2). In discontinuous mode, the pump is precharged before the stimulation and stopped during the stimulation. Obviously, this assumes that the capacitances are sufficiently high (a few microfarads) to be able to provide the charge corresponding to a stimulation. These capacitances can accordingly be external to the ASIC. In discontinuous mode, the state of the signals Phi1 and Phi2 determines the voltage values VHTi available at the input of the multiplexer MUX. The following table provides an example of voltage values VHTi as a function of the respective states of the signals Phi1 and Phi2:

| Phi1/Phi2 | VHT1 | VHT2 | VHT3 | VHT4 | VHT5 | VHT6 |
|---|---|---|---|---|---|---|
| 0/1 | Vdd | Vdd | 3 Vdd | 3 Vdd | 5 Vdd | 5 Vdd |
| 1/0 | Vdd | 2 Vdd | 2 Vdd | 4 Vdd | 4 Vdd | 6 Vdd |

Reference will now be made to FIGS. 6 to 18 to describe an embodiment of the output stage ES, also referred to as the current distribution device.

As is shown in FIG. 6, the output stage ES can, for example, be composed of four parts: a reconfigurable multi-output current mirror MC, a discharge control device DCD, a voltage monitoring device DST and a network of capacitors RCAP.

Unless otherwise indicated, the term "current mirror" will be used hereinafter to refer to the reconfigurable multi-output current mirror MC. Moreover, as indicated hereinbefore, the number (n=4) of cathodes Ki shown in FIG. 6 is merely a non-limiting example, the invention being applicable to any excitation device having at least one anode and at least two cathodes.

The voltage monitoring device DST is connected to the outputs K'i of the current mirror MC in order to measure the voltages respectively present at its terminals. These measures are sent, via the cluster of signals RA, to the digital controller CN. The digital controller can use this information to adjust the anode polarization of the multipolar electrode EM, via the high-voltage supply module AHT described hereinbefore, in order to minimize the dissipated power in the current mirror MC, while at the same time allowing it to operate at the optimum output polarization. Moreover, the digital controller CN can deduce from these measurements the impedance Zi of each electrode Ki, as it knows the imposed stimulation current and the output voltage of the high-voltage supply module AHT.

This voltage monitoring device DST can be configured in the form of a network of analogue/digital converters, but it can also be configured, much more simply, in the form of a network of n voltage comparators (n being the number of cathodes of the multipolar electrode EM) comparing the n output voltages of the current mirror MC relative to a common reference voltage generated internally or else externally imposed. In the case of a network of n comparators, the cluster RA simply consists of the n output logic signals of said comparators.

The digitally controlled anode powering is associated with a voltage threshold detection at the terminals of the current sources controlling the cathodes Ki, so as indirectly to measure the voltage at the terminals of the multipolar electrode EM and to deduce therefrom the impedance thereof, in the knowledge of the values of the currents imposed by the current mirror MC. This obviates the need for the use of an analogue/digital converter by the cathode Ki combined with a differential measurement by means of a high-voltage pole on the side of the anode A; this would consume a large amount of power and would take up a good deal of space on an integrated circuit. This also allows evaluation of the impedances viewed at each cathode Ki. For example, identification of a first-order electrode model necessitates a time counter and only three measurements.

One of the main constraints placed on a stimulation device is that the average of the stimulation current in each cathode is zero, under the threat of causing lesions at the stimulation site. The network of capacitors RCAP therefore preferably consists of n capacitors (n being the number of cathodes of the multipolar electrode EM) placed in series with each of the cathodes Ki of the multipolar electrode.

At the end of a stimulation, the capacitors forming the network of capacitors RCAP have stored a charge representative of the integral of the stimulation current having circulated in the attached cathode. The purpose of the discharge monitoring device DCD, if it is provided, is therefore to establish a conduction path between each of the points K'i and the anode A of the multipolar electrode EM. There ensues an inversion of the roles of the cathode Ki and the anode A of the multipolar electrode EM and the circulation of currents passing from the cathodes Ki (therefore acting in this case as anodes) to the anode A (therefore acting in this case as cathodes) under the effect of the power stored in the capacitors of the network RCAP. When the capacitors are discharged, there has circulated in each cathode Ki, during the discharge phase, a current, the integral of which is the exact opposite of the integral of the stimulation current, over a stimulation/discharge cycle. The average value of the stimulation current is therefore zero.

The discharge current preferably cannot be interpreted as a stimulation. As the nerve tissues have a recovery phase, which immediately follows a stimulation and during which the tissues are insensitive to the stimulations, the amplitude of which remains below that of the initial stimulation, the discharge control device DCD is therefore preferably configured to allow each discharge current to be limited to a fraction, for example equal to 10%, of the maximum amplitude of the stimulation current supplied to the corresponding (or associated) output K'I.

FIG. 7 shows an embodiment of a discharge control device DCD of this type in the case of a multipolar electrode EM having two cathodes K1, K2.

In this example, the signals SA, SB and SC form the cluster CD of FIGS. 2 and 6. They are provided by the digital controller CN, optionally through logic-level adapters which are powered by the anode A and provide voltages capable of appropriately blocking the transistors.

FIG. 8 shows non-limiting examples of time charts defining the time characteristics of the current I passing through the multipolar electrode EM (for the sake of simplicity, it has been assumed that the electrode comprises merely a single cathode and that the anode current is therefore equal to the cathode current) and control signals SA, SB and SC. In these time charts, Imx and −Idech denote the maximum value and the minimum value of the current I respectively, Tstim denotes the duration of the stimulation, Tneutre denotes the time separating the stimulation phase from the discharge phase, Tdech denotes the duration of the discharge phase, and the moments TA, TB and TC are the moments for activation (activation of conduction) of the transistors MiA, MiB and MiC.

This figure, FIG. 8, shows logic levels for SA, SB and SC such that a logic level "1" corresponds to the conduction of the controlled transistor and a logic level "0" corresponds to the blocking of this transistor. These are therefore not voltage levels. Furthermore, in the time chart of the current I, the scale for I<0 has deliberately been enlarged to account more accurately for the development of I during the discharge phase.

The moment TA coincides with the start of the discharge phase (end of the neutral time). The moments TB and TC, like the resistances RA and RB, can, for example, be chosen, as indicated hereinafter, with Tstmx denoting the maximum duration of a stimulation, α denoting the maximum value of the (Idech/Imx) ratio and C denoting the value of a capacitor of the network RCAP, and the maximum amplitude stimulation Imx, leading to the largest amount of charge stored in the capacitor, being a rectangular pulse of amplitude Imx and duration Tstmx:

Idech=(I×Tstmx)/(C×RA). The constraint placed on the maximum value of Idech then leads to RA=Tstmx/(α×C), TB can be chosen such that TB−TA=Tdech−Tstmx/α the resistance RB is deduced from the choice of TB in order to comply with the constraint placed on the maximum value of Idech: RB=RA/(exp(αTdech/Tstmx−1)−1), TC can be chosen such that TC−TB=Tstmx(1−exp(1−αTdech/Tstmx−1))/α, RC=RA exp(1−αTdech/Tstmx)/(exp(exp(αTdech/Tstmx−1)−1)−1).

The resistance values thus obtained correspond to transistors having an ideal switch behaviour. It is therefore expedient, during the production of the discharge control device DCD, to deduct from these resistances the resistance in the on-state (Ron) of the transistors. Moreover, in order to reduce the number of integrated components, the resistance RC can be eliminated and the transistors designed so that the resistance thereof in the on-state (Ron) is equal to RC.

Merely by way of example, if Tstmx=1 ms, Tdech=20 ms, α=0.1 and C=2 μF, the following can be chosen: RA≈5 kΩ, RB≈3 kΩ, RC≈400Ω, TB−TA≈10 ms and TC−TB≈6 ms. Moreover, the duration of the neutral time is short, typically of the order of one hundredth of a microsecond.

At the time of the stimulation, the main purpose of the output stage ES is to impose on each of the n cathodes Ki of the multipolar electrode EM a current Iki proportional to the current Idac provided to it by the digital/analogue converter DAC. It must also be possible for the Iki/Idac ratio to be chosen, for each cathode Ki, by the digital controller CN via the signals of the cluster Cfg shown in FIG. 2.

FIG. 9 illustrates schematically, in the case of a multipolar electrode EM having four cathodes, wound around a nerve, the benefit of the choice of the Iki/Idac ratios for spatially selecting the nerve fibres to be stimulated and the importance of the stability of the Iki/Idac ratios if Idac varies (the changes in the amplitude of the stimulation must not induce change in the spatial location of the stimulation). A reconfigurable multi-output current mirror MC fulfills this main purpose of the output stage ES.

A reconfigurable multi-output current mirror MC can consist of a set of basic devices. The term "basic device" refers in the present context to:

a voltage/current converter CTC, or
a current/voltage converter CCT, or
a controllable voltage/current converter CTTC, or
a voltage/current converter with programmable transconductance CTCTP, or
a balanced current distributor RCE, or
a controllable balanced current distributor RCEC, or
a multi-output current mirror MCMS.

Some of these basic devices will now be described by way of non-limiting examples using mainly, but not exclusively, field effect transistors (FETs) with an N channel and an insulated gate. Similar examples based, for example, on P channel field effect transistors (FETs) or bipolar transistors are also conceivable.

The term "voltage/current converter CTC" refers in the present context to an electronic device having at least three terminals: an input terminal E, an earth terminal M and an output terminal S absorbing a current Is.

The potential differences appearing respectively between the pin S and the pin M, on the one hand, and the pin E and the pin M, on the other hand, will be denoted hereinafter by Vsm and Vem.

The operating range of the voltage/current converter CTC is defined by two voltages Vmax and Vmin. The voltage/current converter CTC is in the present context considered to be within its operating range if Vmin<Vsm<Vmax. Moreover, within its operating range, the voltage/current converter CTC has to satisfy the condition Is=g(Vem)+Go VSM, wherein g( ) is a monotonic function and Go is the output conductance thereof.

The behaviour of this voltage/current converter CTC is all the more satisfactory in view of the fact that Go Vsm is small relative to g(Vem) and that the function g( ) approximates a linear function. Moreover, it is desirable for the input resistance viewed between the terminals E and M to be as high as possible.

Optionally, a voltage/current converter CTC can have additional input terminals intended, inter alia, to receive polarization voltages or currents.

FIGS. 10A and 10B show two non-limiting embodiments of a voltage/current converter CTC comprising field effect transistors (FETs) with an N channel and an insulated gate. In FIG. 10B, the terminal Vref represents an input intended to receive a polarization voltage.

The term "current/voltage converter CCT" refers in the present context to an electronic device having at least three terminals: an input terminal E absorbing a current Ie, an earth terminal M and an output terminal S. The main purpose of a device of this type is to generate a potential difference Vsm between its terminal S and its terminal M satisfying the condition Vsm=f(Ie), wherein f( ) is a monotonic function.

The behaviour of this current/voltage converter CCT is all the more satisfactory in view of the fact that the function f( ) approximates a linear function. Moreover, it is desirable for the input resistance viewed between the terminals E and M to be as small as possible.

Optionally, a current/voltage converter CCT can have additional input terminals intended, inter alia, to receive polarization voltages or currents, and/or additional output terminals providing either further voltage images of the input current Ie or, more generally, further (voltage or current) images of the input or polarization variables.

FIGS. 11A to 11C show three non-limiting embodiments of a current/voltage converter CCT comprising field effect transistors (FETs) with an N channel and an insulated gate. In FIG. 11B, the terminal Vref represents an input intended to receive a polarization voltage. Furthermore, in FIG. 11C, the terminal S' is an additional output providing a second image voltage of the input current Ie.

A comparison of FIGS. 10 and 11 reveals that a current/voltage converter CCT can be obtained from a voltage/current converter CTC to which voltage feedback is applied.

The term "controllable voltage/current converter CTCC" refers in the present context to a device having at least four terminals: an input terminal E, an earth terminal M, a control terminal C receiving a logic signal and an output terminal absorbing a current Is.

The potential differences appearing respectively between the pin S and the pin M, on the one hand, and the pin E and the pin M, on the other hand, will be denoted hereinafter by Vsm and Vem.

The operating range of the controllable voltage/current converter CTCC is defined by two voltages Vmax and Vmin. The controllable voltage/current converter CTCC is in the present context considered to be within its operating range if Vmin<Vsm<Vmax. Moreover, within its operating range, the controllable voltage/current converter CTCC has to satisfy the following conditions:

if the control terminal C is at logic level "0", Is=0, regardless of the values of Vem and Vsm, and if the control terminal C is at logic level "1", the controllable voltage/current converter CTCC behaves like a voltage/current converter CTC.

Optionally, a controllable voltage/current converter CTCC can also have additional input terminals intended, inter alia, to receive polarization voltages or currents, and/or a complementary control terminal C* intended to receive a logic signal complementary to that received by the control terminal C.

FIGS. 12A to 12C show three non-limiting embodiments of a controllable voltage/current converter CTCC. In FIGS. 12B and 12C, the terminal Vref is an input intended to receive a polarization voltage. FIG. 12C is identical to FIG. 12B except for the fact that the transistor M1 is in this case a P channel field effect transistor (FET); this allows the control terminal C to be dispensed with but means that the voltage Vref is necessarily higher than the threshold voltage of the transistor M1. The terminal Vdd is, moreover, a polarization voltage for the substrate of the transistor M1.

From the point of view of size, the transistors M0 and M1, which are used in switching, can be "cut down" to the minimum allowed by the technology with regard to the width and length of the channel. Conversely, it is preferable to give the channels of the transistors M2 and M3 lengths and widths much greater than the minimum in order to minimize the influence of their noise and to improve the matching thereof among a plurality of controllable voltage/current converters CTCC.

The term "voltage/current converter with programmable transconductance CTCTP" refers in the present context to an electronic device having at least p+3 terminals: an input terminal E, an earth terminal M, an output terminal S absorbing a current It and a control bus C[1:p] receiving logic signals.

The potential differences appearing respectively between the pin S and the pin M, on the one hand, and the pin E and the pin M, on the other hand, will be denoted hereinafter by Vsm and Vem.

The operating range of the voltage/current converter with programmable transconductance CTCTP is defined by two voltages Vmax and Vmin. The voltage/current converter with programmable transconductance CTCTP is in the present context considered to be within its operating range if Vmin<Vsm<Vmax. Moreover, within its operating range, the voltage/current converter with programmable transconductance CTCTP has to satisfy the condition It=N g(Vem)+Go Vsm, wherein N is the digital value coded by the control bus, g( ) is a monotonic function and Go is the output conductance of the voltage/current converter with programmable transconductance CTCTP, which output conductance is optionally a function of n. A plurality of codings are conceivable, and in particular the natural binary code or else a non-minimal code such as, for example, the number of signals carried in logic state "1".

As is illustrated schematically in FIG. 13, a voltage/current converter with programmable transconductance CTCTP can be produced by combining p controllable voltage/current converters CTCC, as indicated hereinafter:

the input terminal E of each of the p controllable voltage/current converters CTCC is connected to the input terminal E of the voltage/current converter with programmable transconductance CTCTP, the output terminal S of each of the p controllable voltage/current converters CTCC is connected to the output terminal S of the voltage/current converter with programmable transconductance CTCTP (the current It is in this case equal to the sum of the currents Is absorbed by each of the controllable voltage/current converters CTCC), the earth terminal M of each of the controllable voltage/current converters CTCC is connected to the earth terminal M of the voltage/current converter with programmable transconductance CTCTP, the control terminal of each of the controllable voltage/current converters CTCC is connected to precisely one signal from the control bus C[1:p] of the voltage/current converter with programmable transconductance CTCTP, if the controllable voltage/current converters CTCC have additional input terminals, these will be wired in such a way that all of the controllable voltage/current converters CTCC have the same behaviour, if the controllable voltage/current converters CTCC have a complementary control terminal C*, then the voltage/current converter with programmable transconductance CTCTP has to have a complementary control bus C*[1:p], and the code used for encoding the digital input value of the voltage/current converter with programmable transconductance CTCTP is the number of signals carried in logic state "1" in the control bus.

It is also possible to produce a voltage/current converter with programmable transconductance CTCTP using the natural binary code with ($2^p-1$) controllable voltage/current converters CTCC. In this case, the signal C[1] is connected to a single controllable voltage/current converter CTCC, the signal C[2] is connected to precisely two controllable voltage/ current converters CTCC, the signal C[3] is connected to precisely four controllable voltage/current converters CTCC, and so on up to the signal C[p] which is connected to $2^p-1$ controllable voltage/current converters CTCC.

The term "balanced current distributor RCE" refers in the present context to a device with p+1 terminals having: an input terminal E providing a current Ie and a bus of outputs S[1:p], each absorbing a current ISi. Additional terminals other than those presented can be envisaged hereinafter in order to provide the device with polarization voltages or currents and also with earth.

The potential difference between the output terminal S[i] and the input terminal E will be denoted hereinafter by VSi.

The (convex) range of operating voltages of the balanced current distributor RCE is defined by Vmin<VSi<Vmax (Vmin and Vmax being two voltages having the same sign satisfying Vmin<Vmax), whatever the value of i, an integer pertaining to the interval [1, p]. Moreover, the behaviour of the balanced current distributor RCE is defined by the equation ISi=Ie/p, whatever the value of I, an integer pertaining to the interval [1,p].

In order for the operation of this distributor to be satisfactory, it has to have an input resistance that is as low as possible and output resistances that are as high as possible.

FIG. 14 shows schematically, by way of non-limiting example, an embodiment of a balanced current distributor RCE comprising N channel field effect transistors.

With regard to size, the transistors Mi used all have a single width and a single length, which are preferably non-minimal in order to improve the matching of the transistors.

In FIG. 14, Vref represents a reference voltage and M represents an earth terminal corresponding to the polarization of the substrate of the transistors.

The term "controllable balanced current distributor RCEC" refers in the present context to a device with 2p+1 terminals having: an input terminal E providing a current Ie, a bus of outputs Sr[1:p] each absorbing a current ISi and a control bus C[1:p] receiving logic signals.

The potential difference between the output terminal S[i] and the input terminal E will be denoted hereinafter by VSi, and the number of control inputs receiving a logic signal at "1" by N.

The (convex) range of operating voltages of the controllable balanced current distributor RCEC is defined by Vmin<VSi<Vmax (Vmin and Vmax being two voltages having the same sign satisfying Vmin<Vmax), whatever the value of i, an integer pertaining to the interval [1, p]. Furthermore, the behaviour of the controllable balanced current distributor RCEC is defined by the following conditions:

if C[i] is at logic level "0", then ISi=0, and
if C[i] is at logic level "1", then ISi=Ie/N.

Optionally, a controllable balanced current distributor RCEC can also have additional input terminals intended, inter alia, to receive polarization voltages or currents, and/or a complementary control bus C*[1:p] intended to receive logic signals complementary to those received by the bus C[1:p].

FIGS. 15A and 15B show schematically, by way of non-limiting example, two embodiments of a controllable balanced current distributor RCEC comprising field effect transistors. The example illustrated in FIG. 15A uses merely N channel transistors. It requires 2p control inputs (C[1:p] and C*[1:p]) and the voltage Vref is limited to Vdd less a threshold voltage of an N channel transistor (Vdd being the voltage corresponding to a high logic level on the control inputs).

The example shown in FIG. 15B uses N channel transistors and P channel transistors. p control inputs are sufficient. It is, however, necessary to add a polarization voltage (Vdd) for the substrates of the P channel transistors. Moreover, the device is operative merely for a voltage Vref greater than a P channel transistor threshold voltage. By way of these two examples, there can be constructed another variation, less constraining in terms of deviation from Vref, by replacing the transistors Mi1 with CMOS transmission gates consisting of an N channel transistor and a P channel transistor placed in parallel at the drains and sources thereof and controlled by complementary signals at the gates thereof.

With regard to size, the transistors Mi0 and Mi1, used in switching, are at the minimum allowed by the technology, whereas the transistors Mi2 all have a single width and a single length, which are preferably non-minimal so as to improve the matching of the transistors.

In FIGS. 15A and 15B, Vref represents a reference voltage and M represents an earth terminal corresponding to the polarization of the substrate of the N channel transistors, and Vdd is used for the polarization of the substrates of the P channel transistors.

The term "multi-output current mirror MCMS" refers in the present context to an electronic device with p+2 terminals having: an earth terminal M, an input terminal E and an output bus S[1:p]. Additional terminals other than those presented can be envisaged hereinafter in order to provide the device with polarization voltages or currents, in particular.

The current absorbed by the input terminal E will be denoted hereinafter by Ie, the current absorbed by the output terminal S[i] by ISi, and the potential difference between S[i] and M by VSi.

The (convex) range of operating voltages of the multi-output current mirror MCMS is defined by Vmin<VSi<Vmax (Vmin and Vmax being two voltages having the same sign satisfying Vmin<Vmax), whatever the value of i, an integer pertaining to the interval [1, p]. Furthermore, the behaviour of the multi-output current mirror MCMS is defined by the condition Isi=Ai Ie+Gi VSi+{sum of j=1 to p of the Gij(VSi−VSj)}, wherein Ai represents the current amplification of the branch i of the multi-output current mirror MCMS, Gi represents the output conductance of the branch i of the multi-output current mirror MCMS and Gij represents the differential output conductance between the branches i and j of the multi-output current mirror MCMS.

The term "reconfigurable multi-output current mirror MC" refers in the present context to a multi-output current mirror MCMS for which the current amplifications of each branch (Ai) can be chosen during operation.

A mirror of this type is an electronic device with (p(q+1)+2) terminals having: an earth terminal M, an input terminal E, an output bus S[1:p] and a control bus CA[1:p][1:q]. Additional terminals other than those presented can be envisaged hereinafter in order to provide the device with polarization voltages or currents, in particular.

Each control sub-bus CA[i][1:q] regulates the current amplification of a single (output) branch of the reconfigurable multi-output current mirror MC. The coding of this sub-bus and also the influence thereof on the amplification Ai depend on the embodiment of the reconfigurable multi-output current mirror MC.

Two classes of reconfigurable multi-output current mirror MC can be defined: the class of modular reconfigurable multi-output current mirrors and that of distributor-type reconfigurable multi-output current mirrors.

As is illustrated schematically in FIG. 16, a modular reconfigurable multi-output current mirror is formed by combining a current/voltage converter CCT, as defined hereinbefore, with p voltage/current converters with programmable transconductance CTCTP, as defined hereinbefore.

This combination can be provided as follows:
the input terminal E of the current/voltage converter CCT is connected to the input terminal E of the modular reconfigurable multi-output current mirror MC,
the earth terminal M of the current/voltage converter CCT and also the earth terminals M of the p voltage/current converters with programmable transconductance CTCTP are connected to the earth terminal M of the modular reconfigurable multi-output current mirror MC,
the input terminal E of each of the voltage/current converters with programmable transconductance CTCTP is connected to the output terminal S of the current/voltage converter CCT,
the output terminal S of each of the p voltage/current converters with programmable transconductance CTCTP is connected to precisely one output S[i] of the modular reconfigurable multi-output current mirror MC, and
each control sub-bus CA[i][1:p] of the modular reconfigurable multi-output current mirror MC is connected to the control bus C[1:p] of the voltage/current converter with programmable transconductance CTCTP, the output S of which is connected to the output S[i] of the modular reconfigurable multi-output current mirror MC.

The coding of the control sub-buses CA[i][1:q] is then chosen by the architecture of the voltage/current converter with programmable transconductance CTCTP, as indicated hereinafter:
let Iti be the current absorbed by the output terminal S[i],
let Ie be the current absorbed by the input terminal E (of the modular reconfigurable multi-output current mirror MC),
let VSi be the potential difference between the terminal S[i] and the terminal M,
let Ni be the digital value coded by the control sub-bus CA[i][1:q] (as indicated in the preceding definition of the voltage/current converter with programmable transconductance CTCTP),
let Vs=f(Ie) be the equation characterizing the transresistance of the current/voltage converter CCT,
let It=N g(Vem)+Go Vsm be the equation characterizing the transconductance of a voltage/current converter with programmable transconductance CTCTP.

Furthermore, the behaviour of the modular reconfigurable multi-output current mirror MC is described by the equation Iti=Ni g(f(Ie))+Gi VSi+{sum of j=1 to p of the Gij(VSi−VSj)}.

A comparison of this expression with that defining the behaviour of a multi-output current mirror MCMS reveals that the functions f and g must be such that their composition provides a linear function, at least for the useful input current range. The architecture of the current/voltage converter CCT and that of the voltage/current converters with programmable transconductance CTCTP accordingly have to be matched. In order to do this, use can be made, for example, of a current/voltage converter CCT of the type of that shown in FIG. 11A with a voltage/current converter with programmable transconductance CTCTP produced by combining controllable voltage/current converters CTCC of the type of that shown in FIG. 12A. For example, the current/voltage converter CCT shown in FIG. 11B can equally well be used with the controllable voltage/current converters CTCC shown in FIGS. 12B and 12C.

As is illustrated schematically in FIG. 17, a distributor-type reconfigurable multi-output current mirror is produced by combining a current mirror, consisting of a current/voltage converter CCT and a voltage/current converter CTC, with a controllable balanced current distributor RCEC having m outputs.

This combination can be provided as follows:
the input terminal E of the current/voltage converter CCT is connected to the input terminal E of the distributor-type reconfigurable multi-output current mirror MC, and Ie is the current absorbed by this terminal,
the earth terminal M of the current/voltage converter CCT and also the earth terminals M of the voltage/current converter CTC and the controllable balanced current distributor RCEC are connected to the earth terminal M of the distributor-type reconfigurable multi-output current mirror MC,
the input terminal E of the controllable balanced current distributor RCEC is connected to the terminal S of the voltage/current converter CTC, and Is is the current absorbed by the voltage/current converter CTC on its terminal S,
the control bus of the distributor-type reconfigurable multi-output current mirror MC CA[1:p][1:q] is connected, in a manner which will be specified hereinafter, to the control bus C[1:m] of the controllable balanced current distributor RCEC, and
the output bus S[1:p] of the distributor-type reconfigurable multi-output current mirror MC is connected, in a manner which will be specified hereinafter, to the output bus Sr[1:m] of the controllable balanced current distributor RCEC.

With regard to the combination of the voltage/current converter CTC and the controllable balanced current distributor RCEC, N denoting the number of signals carried in logic state '1' in the bus C[1:m], Isri the current absorbed by the output Sr[i] of the controllable balanced current distributor RCEC, Vs=f(Ie) the equation characterizing the transresistance of the current/voltage converter CCT, and Is=g(Vem) the equation characterizing the transconductance of the voltage/current converter CTC, and disregarding the effects of the output conductances, which are necessarily finite, the following equations are obtained:

$$Is=g(f\{Ie\})) \qquad (1)$$

$$Is=\{\text{sum of } j=1 \text{ to } m \text{ of the } Isri\} \qquad (2)$$

$$Isri=Is/N \text{ if } Cr[i]=\text{'1'}, \text{ if not } 0 \qquad (3)$$

A comparison of these expressions with those defining the behaviour of a reconfigurable multi-output current mirror reveals that the functions f and g must be such that their composition provides a linear function, at least for the useful input current range. The architectures of the current/voltage converter CCT and the voltage/current converter CTC accordingly have to be matched. In order to do this, use can be made, for example, of a voltage/current converter CCT of the type of that shown in FIG. 10A with a current/voltage converter CCT of the type of that shown in FIG. 11A. For example, the voltage/current converter CCT shown in FIG. 10B can equally well be used with the current/voltage converters CCT shown in FIGS. 11B and 11C.

It may also be noted that the sum of the output currents of the distributor-type reconfigurable multi-output current mirror MC is not configurable. It depends merely on the input current and the current amplification of the basic mirror formed by the combination of the voltage/current converter CTC and the current/voltage converter CCT.

Furthermore, it may also be noted that the interconnections of the control buses and the output buses depend on the coding adopted for representing the digital values on the control sub-buses CA[i][1:q]. Two purely illustrative and non-limiting examples of the distributor-type reconfigurable multi-output current mirror MC for a coding of the "number of signals at '1'" type and for a natural binary coding will be provided hereinafter.

By replacing the equation (1) Is=g(f(Ie)) with the equation Is=A Ie and by calling Ni the digital value coded by the control sub-bus CA[i][1:q], there is obtained the equation ISi=Ni A Ie/{sum of j=1 to p of the Ni} which defines the operation of a distributor-type reconfigurable multi-output current mirror MC.

In order to produce a distributor-type reconfigurable multi-output current mirror MC for a coding of the "number of signals at '1'" type, use is made of a controllable balanced current distributor RCEC having m=pq outputs. Each of the p outputs S[i] of the distributor-type reconfigurable multi-output current mirror MC has to be connected to precisely q outputs of the controllable balanced current distributor RCEC. Moreover, the q signals from the sub-bus CA[i][1:q] have to be connected to the q control signals from the controllable balanced current distributor RCEC that control the outputs connected to S[i]. There can, for example, be produced a first set of connections in which all of the signals from the bus segment Sr[(i−1)q+1:iq] are connected to S[i] and a second set of connections in which the bus segment C[(i−1)q+1:iq] is connected to the sub-bus CA[i][1:q].

In order to produce a distributor-type reconfigurable multi-output current mirror MC for a natural binary coding, use is made of a controllable balanced current distributor RCEC having m=p($2^q$−1) outputs. Each of the p outputs S[i] of the distributor-type reconfigurable multi-output current mirror MC has to be connected to precisely ($2^q$−1) outputs of the controllable balanced current distributor RCEC. Moreover, the q signals from the sub-bus CA[i][1:q] have to be connected to the ($2^q$−1) control signals from the controllable balanced current distributor RCEC that control the outputs connected to S[i]:CA[i][1] connected to one control signal, CA[i][2] connected to two control signals, CA[i][3] connected to four control signals and, more generally, CA[i][j] connected to $2^{(j−1)}$ control signals. There can, for example, be produced a first set of connections in which all of the signals from the bus segment Sr[(i−1)($2^q$−1)+1:i($2^q$−1)] are connected to S[i] and a second set of connections in the signals from the bus segment C[(i−1)($2^q$−1)+$2^{(j−1)}$:(i−1)($2^q$−1)+$2^j$−1] are connected to the signal CA[i][j]. CA[i][q] denotes in this case the most significant bit of the binary representation.

At the time of the stimulation, the main purpose of the output stage ES is to impose on each of the n cathodes Ki of the multipolar electrode EM a current Iki proportional to the current Idac provided to it by the digital/analogue converter DAC. It must also be possible for the Iki/Idac ratio to be chosen, for each cathode Ki, by the digital controller CN via the signals of the cluster Cfg shown in FIG. 2. In the illustrated example, n=4 (i=1 to 4); however, as indicated hereinbefore, it can assume any value equal to or greater than 2.

Generally, the current mirror MC of the invention can be in the form of a reconfigurable multi-output current mirror having n outputs. As is shown in FIG. 6, the current mirror MC is interconnected to the other elements of the output stage ES by its control bus CA which forms the cluster Cfg, its input E being connected to the signal Idac and its outputs S[1:n] being respectively connected to the signals K'i.

The current Ist, which circulates in the anode A of the multipolar electrode EM, represents the sum of the currents Iki circulating in the various cathodes Ki. It is important to note that this current Ist is not necessarily distributed equally between the n different cathodes Ki, so that each of them has a current equal to Ist/n. Indeed, it must be possible to distribute this current Ist unequally between the n different cathodes Ki or else merely between some of them.

For example, in the presence of four cathodes K1 to K4 (n=4), there can be distributions of the type (¼, ¼, ¼, ¼), or (¼, ¼, ½, 0), or else (¼, 0, 0, ¾), or else (⅓, ⅓, ⅓, 0), or else (0, ⅓, 0, ⅔), or else (⅕, ⅕, ⅖, ⅕), or else (⅖, 0, ⅗, 0), or else (⅙, ⅙, 2/6, 2/6), and also all possible permutations. These various distributions allow the spatial location of the stimulation in the nerve to be controlled.

In order to separate the commands allowing the stimulation to be located from those controlling the amplitude thereof, it can be prescribed that the Ist/Idac ratio is not configurable, i.e. that a change in distribution does not modify the amplitude of the overall stimulation pulse (measured at the anode A of the multipolar electrode EM). It is the digital controller CN that, by the commands that it applies to the current mirror CM, sets the current distributions. These commands also enable it to specify the moments before the start and end of stimulation.

There will be described hereinafter, by way of example, a current mirror MC intended to be used with a multipolar electrode EM having four cathodes K1 to K4 and for current distributions consisting of combinations of the values {0, ¼, ⅓, ½, ⅔, ¾, 1}, taken 4 by 4 and such that the sum of the elements of each combination is equal to unity. Moreover, an Ist/Idac ratio equal to four is set.

In the presence of the constraint on the stability of the Iki/Idac ratio, it is preferable to use a distributor-type reconfigurable multi-output current mirror MC of the type of the shown in FIG. 18.

In this example, the Ist/Idac ratio equal to four is obtained by prescribing that the transistors M00, M01, M02, M03 and M04 are all of the same size (and that they are designed and placed on the substrate in accordance with the rules of the art so as to maximize matching thereof).

The number m of outputs of the controllable balanced current distributor RCEC is determined by considering that it must always have the same number r of active outputs in order always to set the same output voltage at the voltage/current converter CTC in order to improve stability at the current Ist during distribution changes. As the smallest common multiple of 4, 3 and 2 is 12, there must accordingly be chosen a controllable balanced current distributor RCEC comprising 4×12=48 outputs that is controlled so as permanently to provide 12 active outputs. It may be noted in passing that this choice allows the range of values which can be used in the distributions to be broadened, producing the following range: {0, ⅙, ¼, ⅓, ½, ⅔, ¾, ⅚, 1}.

The cluster Cfg derived from the digital controller CN therefore consists of 48 logic signals organized into four sub-buses, each having 12 signals. The number of signals carried in logic state "1" (active signals) on a sub-bus represents the number of twelfths of total stimulation current that are applied to the corresponding cathode. However, this is not the case if the total number of active signals on the cluster Cfg is precisely equal to 12.

The digital controller CN can also use the signals of the cluster Cfg to block the cathodes Ki outside the stimulation moments.

The controllable balanced current distributor RCEC shown in FIG. 18 is substantially identical to that described hereinbefore with reference to FIG. 15B. Its voltage Vref therefore cannot be less than a P channel transistor threshold voltage. However, use can be made instead of an RCEC distributor of the type of that described hereinbefore with reference to FIG. 15A, but in this case the bus Cfg has to carry 96 signals unless the signals are supplemented at the current mirror MC. It is even conceivable to delocalize a portion of the functions of the digital controller CN at the current mirror MC and to transmit merely coded instructions to the cluster Cfg.

In order to improve the matching of the current/voltage converter CCT and the voltage/current converter CTC, use is preferably made of the same reference voltage Vref for the current/voltage converter CCT and for the controllable balanced current distributor RCEC. Moreover, so that the transistors M0i are placed under conditions that are as similar as possible with regard to their drain/source potential difference, the transistor M100 is passed through by the current Idac, whereas 12 transistors of the controllable balanced current distributor RCEC are passed through by a current equal to 4×Idac. The transistor M100 accordingly has to have a channel length identical to that of the transistors M101 to M148 and a channel width equal to three times that of said transistors M101 to M148.

This distributor structure has a relatively high inter-electrode output conductance value (whereas the common-mode output conductance is very low on account of the cascode structure implicit to this device). In order to remedy this drawback, use can be made, in a variation, of a modular reconfigurable multi-output current mirror MC comprising four voltage/current converters with programmable transconductance CTCTP having 12 inputs. The separation of the basic current mirrors completely eliminates inter-electrode output conductance at the cost of a slight increase in common-mode conductance and a slightly increased risk of dispersion of the characteristics from one output to the other.

As stated hereinbefore, the invention also proposes a communication protocol adapted to wireless transmissions between the controller CR and the implants I (or distributed stimulation units USRs), of the type of that described hereinbefore, of a stimulation system.

Obviously, the invention is not limited merely to transmissions by way of waves between the controller CR and the implants I (or USR). A wired bus transmission mode is conceivable without the proposed protocol losing its relevance.

In the presence of wireless transmissions (i.e. by way of waves), acknowledgement is the only way of being sure that a frame of data packets has been properly received. The mode of access to the medium is also important. The method for accessing the medium and the model for cooperation between the various entities forming the stimulation system are closely linked. Collisions, on the other hand, are not necessarily detected.

Preferably, the logical links between the physically related entities are managed in a connectionless manner, with acknowledgement on request and without flow control.

On account of the type of environment considered in the described example (intracorporeal), a compromise must be found between reliability during the exchange of frames and the complexity of the transmissions.

Firstly, it is necessary, in certain cases, to be sure that a frame sent has indeed been received, or even that an operation instructed by the controller CR (in a transmitted request) has indeed been carried out, in particular when the body being stimulated is that of a human.

It is accordingly advantageous to allow the controller CR to request an acknowledgement in certain specific situations (i.e. non-systematically). For example, provision may be made to prevent data from being exchanged unless an acknowledgement has been received by the controller CR. This allows a flow control to be avoided.

Establishing a connection ensures, in general terms, that the nodes (or relevant entities) are active and that they are able to participate in the communication. Preferably, the nodes of the system are at all times anticipating a frame reception.

If collisions are not detected, it is important to avoid them or to minimize the risk thereof.

Several access methods are conceivable.

A first method, referred to as a static method, consists in imposing on each emitter a time interval during which it is allowed to emit. This can be carried out by time division multiplexing. The access is in this case of the deterministic type.

This static method does not provide efficient exploitation of the medium and leads to systematic consideration of all of the nodes, even the "inactive" ones.

A second method, referred to as a competitive method, consists in allowing each emitter (or distributed stimulation unit USR) to emit when it needs to do so, independently of the others. If two emitters emit simultaneously, a conflict arises and a special procedure has to be implemented to settle the conflict.

With this type of method, it is crucial to limit the risk of collision by controlling the right to speak (DDP) of the nodes of the network. Response to any errors is important but the risks of collision must nevertheless be minimized in order to prevent non-receipt of important messages. The right to speak must accordingly be managed.

A third method, referred to as an elective method, consists in dynamically choosing the emitter. In the case of centralized management, a master node is responsible for taking decisions, whereas in the case of distributed management tokens are exchanged between the nodes. The access is in this case of the probabilistic type.

Centralized management presents the problem of the right to free speech of the slaves, i.e. the various distributed stimulation units (or USRs). Although fairly reliable, systematic polling of all the USRs is not very efficient, given that it induces unnecessary exchanges with the inactive nodes and penalizes the responsiveness of the system. Not all of the USRs are necessarily involved in all of the phases of a movement. Accordingly, in a given configuration, and for a given phase, merely the USRs of a subset have to be active and therefore allowed to express themselves, for example to notify a problem such as a stimulation error.

As this third method is that which is preferred, it will now be described in greater detail.

It is first of all necessary to distinguish between the assignment of a right to speak to a node (individual DDP) and the assignment of a right to speak to a group of nodes (group DDP).

It will be noted that a slave node (in this case a USR) automatically has the right to speak as soon as it is requested that it provide an acknowledgement. The USR can therefore take this opportunity to signal the detection of an error (prior or relative to the carrying-out of an operation under way). It is then up to the master (the controller CR) to allow the USR to describe the error (i.e. to send a vector describing the detected error(s)). This permission is given by way of an individual DDP.

The group DDP is, in particular, intended to allow the active USRs to signal an error without being observed. More specifically, a group DDP is assigned to each group for a chosen time window, so the USRs of each group can emit if they deem it to be necessary.

Preferably, in order to limit the risk of collision within a time window, a time interval is allocated to each USR. Each USR is positioned with respect to time, automatically, as soon as the controller CR has indicated to it that it has assigned a DDP to the group to which the USR belongs. Obviously, each USR knows the group to which it belongs and also its position within the group, which is defined by a level of priority which can differ from one group to another and which defines the position of the time interval allocated to it within the speech time window of the group.

The duration of the time intervals depends on the communication technology held (characteristics of the transmissions in terms of speed, precision of the synchronization of the relevant USRs (delay, jitter), etc.).

FIG. 19 shows, on the right-hand side, an example of the assignment and use of an individual DDP by a USR (in this case USR3) and, on the left-hand side, an example of the assignment of a group DDP. The group consists, in this example, of five USRs, the order of priority of which is, for example, USR5, USR3, USR1, USR2, USR7.

Each USR is positioned in accordance with the time interval D allocated to it within the time window allocated to its group. This positioning is defined by the duration of the time interval D and the level of priority (and therefore the position) of the USR. The start date of the time interval is D*. The small black rectangular boxes represent the individual DDPs, the rectangular box drawn in dot-dash lines represents the DDP of the group, the grey rectangles represent the points of access to the medium by the controller CR, and each reference USRi(g,k) represents USR number i, belonging to group g and having a level of priority k within group g.

It is important to note that emission is possible only if the medium is free. Moreover, it is also important to note that the positioning of a USR is relative. Each USR calculates the start date of its time interval relative to the moment of receipt of the group DDP assignment message sent by the controller CR.

As the propagation time is not necessarily the same for attaining each USR, each USR is associated with a time-constant delay (topology and distances maintained) which constitutes a risk of overlapping of the intervals and induces a risk of collision (non-deterministic access). This risk of collision, associated with the fact that a plurality of USRs can have a DDP simultaneously, is illustrated in FIG. 20.

Each USR therefore has to "reset" its time interval in order to minimize the risk of collision. This risk can also be limited by way of internal boundaries within the time interval.

In order to reset, each USR estimates the transmission time of the message originating from the controller CR. This estimation is carried out, for example, during a start-up phase and at the, invitation of the controller CR. It consists in measuring the round trip time RTT of a message of given length between the USR and the controller CR. The measurement of RTT/2 is assumed to correspond to the outward-bound propagation time of the message, the topology being taken to be fixed and the distances being taken to be maintained during the movements induced by the stimulations.

The resetting with the measurement RTT/2 allows the USRs to position themselves more effectively with respect to one another; however, this resetting positions them incorrectly relative to the start date of the window, as shown in FIG. 21. For example, by thus calculating the start date of the time window, there is carried out "back resetting" which establishes the start date of the interval of USR5 (in this case the first of its group) before its calendar date (i.e. before it receives its assignment). It is therefore advantageous to carry out "front resetting" of a half-period D/2. The controller CR also integrates this front resetting into the determination of the end date of the time window, corresponding to the moment at which it automatically resumes control of the group DDP.

The positioning of the USRs is therefore distributed, owing to the fact that each USR is positioned independently.

Access to the medium, described hereinbefore, can be further optimized. More specifically, it is possible to optimize (or minimize) the "rotation" time of an individual DDP within a group using an anticipation mechanism. In order to do this, the USR having a given level of priority can use its individual DDP if, at the end of a chosen time, the USR having the preceding higher level of priority has not emitted (or at least no frame has been detected during said chosen time). A right to speak with sliding intervals (DDPIG) is then defined.

As is illustrated by way of non-limiting example in FIG. 22, a time interval can be subdivided into two portions: a first portion Di1 (in this case i=1 to 4), referred to as the speech portion, during which the USR can emit an error notification message and a second portion Di2 reserved for any response from the controller CR. The possibility of response from the controller CR, following an error signalling by a USR, is thus favoured by guaranteeing it in each time interval a time for access to the medium during which the USRs do not have the right to emit. However, this second portion Di2 is only reserved if the USR having the current DDP has notified an error.

As is illustrated in FIG. 23, the sliding rule is preferably based on the monitoring of the first portion D(i−1)1 of the preceding time interval. If the medium has been occupied, i.e. if a message has circulated, this means that the preceding USR has used its DDP. The second portion D(i−1)2 of the preceding time interval is accordingly likely to be used in response by the controller CR. In the opposite scenario, i.e. when the first portion D(i−1)1 of the preceding time interval has not been used, each USR causes its time interval to slide on the preceding second portion D(i−1)2, thus using the timeslot reserved for the response of the controller CR. If no USR notifies an error throughout the time window allocated to a group, the time window can therefore be reduced by an equation: $(N-1)/(2N)$, wherein N is the number of USRs belonging to the relevant group.

A plurality of variations of the management of the individual DDPs can be envisaged in the presence of error notification(s) by USRs.

A first variation, illustrated in FIG. 24, can consist in allowing each USR to emit freely within its single time interval, in the knowledge that the error messages are very short messages. The error vector forms two bytes, corresponding to a frame of five bytes.

This first variation provides a fixed and non-extendable DDP assignment time.

A second variation can consist, if it is assumed that the messages are not short, in allowing the master to assign a longer time interval to the relevant node via an individual DDP (then optionally to restore a group DDP). In this case, firstly, the USR in question is awarded a longer time interval and the time intervals of the other USRs are cancelled (but potentially subsequently re-established as a function of the new group DDP allocation).

This second variation gives the master total control over the extension of the duration of each individual DDP.

A third variation, illustrated in FIG. 25, can consist in allowing each USR to declare (or broadcast) during its time interval its free reservation of the group DDP, i.e. the fact that it inhibits the group DDP of the other USRS. Although this reservation of the group DDP is theoretically without time limit (and therefore without size limit), it nevertheless preferably remains under the control of the master, so the master can intervene to reject the reservation. The USR, having carried out a free reservation of the DDP of the group, is also responsible then for releasing said group DDP, and this induces the resetting of the time intervals of the other USRs.

This third variation therefore provides an intermediate solution in which each USR is free to extend the duration of its DDP under the control of the master.

The division of the medium described hereinbefore provides a satisfactory compromise between determinism and responsiveness. It allows a factual-type error notification from the USRs to be supported. However, it is possible to proceed differently, for example by allowing regular notifications from the USRS, by periodic exchange of a type of state descriptor certifying or not certifying correct operation. The assignment of the presented right to speak is unique, since the nodes have only one opportunity to speak. However, recurring assignment is also possible. In this case, the nodes have a "periodic" opportunity to speak, and the controller CR does not have to repeat its assignments. The size of the group has merely to be specified and the USR deduces therefrom the periodicity of its time interval.

The management of the transmissions within the controller CR and the distributed stimulation units (or USRs) can be carried out by way of management modules in the form of electronic circuits, software (or computer) modules, or a combination of software modules and electronic circuits.

The invention is not limited to the embodiments of the current distribution device (or output stage), reconfigurable multi-output current mirrors, control electronics, distributed stimulation unit and stimulation system described hereinbefore, merely by way of example; on the contrary, it encompasses all of the variations conceivable to a person skilled in the art within the scope of the following claims.

The invention claimed is:

1. Device (ES) for distributing power between n cathodes (Ki) of at least one multipolar stimulating electrode (EM) further comprising at least one anode (A), n being equal to or greater than two, characterised in that it comprises a reconfigurable current mirror (MC) comprising n outputs (K'i) capable of being coupled respectively to said n cathodes (Ki) and configured to supply to said n outputs (K'i) n complementary fractions (Iki) of a control current (Idac) having respective chosen values which are substantially constant in the presence of an amplitude variation of said control current (Idac) so as to allow substantially constant spatial locating of the stimulation.

2. Device according to claim 1, characterised in that said reconfigurable multi-output current mirror (MC) is of what is known as the "distributor" type.

3. Device according to claim 2, characterised in that said distributor-type reconfigurable multi-output current mirror (MC) comprises a current/voltage converter (CCT) coupled to a voltage/current converter (CTC) and to a controllable balanced current distributor (RCEC) having m outputs.

4. Device according to claim 3, characterised in that said current/voltage converter (CCT) comprises at least one input terminal (E) capable of absorbing a current (Ie), an earth terminal (M) and an output terminal (S) and is configured to establish a chosen potential difference (Vsm) between said output terminal (S) and said earth terminal (M), as a function of said current (Ie), in that said voltage/current converter (CTC) comprises at least one input terminal (E), an earth terminal (M) and an output terminal (S) capable of absorbing a current (Is), in that said controllable balanced current distributor (RCEC) comprises at least one input terminal (E) capable of supplying a current (Ie), a bus of outputs (Sr[1:m]), each absorbing a current (ISi), and a control bus (C[1:m]) capable of receiving logic signals, and in that said input terminal (E) of said current/voltage converter (CCT) is connected to an input terminal of said distributor-type reconfigurable multi-output current mirror (MC), said earth terminal (M) of said current/voltage converter (CCT) and said earth terminals (M) of said voltage/current converter (CTC) and of the controllable balanced current distributor (RCEC) are connected to an earth terminal (M) of said distributor-type reconfigurable multi-output current mirror (MC), said input terminal (E) of said controllable balanced current distributor (RCEC) is connected to said output terminal (S) of said voltage/current converter (CTC), said control bus (C[1:m]) of said controllable balanced current distributor (RCEC) is connected to a control bus (CA[1:p][:q]) of said distributor-type reconfigurable multi-output current mirror (MC), and said output bus (Sr[1:m]) of said controllable balanced current distributor (RCEC) is connected to an output bus (S[1:p]) of said distributor-type reconfigurable multi-output current mirror (MC).

5. Device according to claim 3, characterised in that said current/voltage converter (CCT) and said voltage/current converter (CTC) have matched architectures.

6. Device according to claim 1, characterised in that said reconfigurable multi-output current mirror (MC) is of the modular type.

7. Device according to claim 6, characterised in that said modular reconfigurable multi-output current mirror (MC) comprises at least two voltage/current converters with programmable transconductance (CTCTP).

8. Device according to claim 6, characterised in that said modular reconfigurable multi-output current mirror (MC) comprises a current/voltage converter (CCT) coupled to p voltage/current converters with programmable transconductance (CTCTP).

9. Device according to claim 8, characterised in that said current/voltage converter (CCT) comprises at least one input terminal (E) capable of absorbing a current (Ie), an earth terminal (M) and an output terminal (S) and is configured to establish a chosen potential difference (Vsm) between said output terminal (S) and said earth terminal (M), as a function of said current (Ie), in that each voltage/current converter with programmable transconductance (CTCTP) comprises at least one input terminal (E), an earth terminal (M), an output terminal (S) capable of absorbing a current (It) and a control bus (C[1:p]) capable of receiving logic signals, and in that i) said input terminal (E) of said current/voltage converter (CCT) is connected to an input terminal (E) of said modular reconfigurable multi-output current mirror (MC), ii) said earth terminal (M) of said current/voltage converter (CCT) and said earth terminals (M) of said p voltage/current converters with programmable transconductance (CTCTP) are connected to said earth terminal M of said modular reconfigurable multi-output current mirror (MC), iii) said input terminal (E) of each of said p voltage/current converters with programmable transconductance (CTCTP) is connected to said output terminal (S) of said current/voltage converter (CCT), iv) said output terminal (S) of each of said p voltage/current converters with programmable transconductance (CTCTP) is connected to one of said outputs (Ki) of said modular reconfigurable multi-output current mirror (MC), and v) said control bus (C[1:p]) of each voltage/current converter with programmable transconductance (CTCTP) is connected to control sub-buses (CA[i][1:p]) of said modular reconfigurable multi-output current mirror (MC).

10. Device according to claim 8, characterised in that said current/voltage converter (CCT) and said p voltage/current converters with programmable transconductance (CTCTP) have matched architectures.

11. Device according to claim 1, characterised in that the ratio (Ist/dac) between the current (Ist) circulating in said anode (A), which is equal to the sum of the currents (Iki) supplied to said outputs (K'i), and said control current (Idac) is configurable.

12. Device according to claim 1, characterised in that the ratio (Ist/Idac) between the current (Ist) circulating in said anode (A), which is equal to the sum of the currents (Iki) supplied to said outputs (K'i), and said control current (Idac) is not configurable.

13. Device according to claims 1, characterised in that it comprises a set of n capacitors (RCAP), each coupling one of said outputs (K'i) to one of said cathodes (Ki).

14. Device according to claims 1, characterised in that it comprises a voltage monitoring device (DST) connected to said outputs (K'i) and configured to measure the voltages respectively present at said outputs (K'i), so they allow adjustment of a polarisation of said anode (A) of the multipolar electrode (EM) via a high-voltage supply module (AHT).

15. Device according to claim 14, characterised in that said voltage monitoring device (DST) comprises a network of analogue/digital converters.

16. Device according to claim 14, characterised in that said voltage monitoring device (DST) comprises a network of n voltage comparators, each configured to compare the n voltages at said outputs (K'i) relative to a common reference voltage.

17. Device according to claim 14, characterised in that said voltage monitoring device (DST) comprises a network of 2n voltage comparators configured in pairs to compare the n voltages at said outputs (K'i) relative to two common reference voltages.

18. Device according to claim 1, characterised in that it comprises a discharge control device (DCD) coupled to said outputs (K'i) and to said anode (A) and configured to establish, at the end of the stimulation, a conduction path between each of said outputs (K'i) and said anode (A), so as to induce a circulation of n discharge currents from said cathodes (Ki) to said anode (A).

19. Device according to claim 13, characterised in that said n discharge currents originate from the n energies respectively stored by said n capacitors of said set (RCAP).

20. Device according to claim 18, characterised in that said discharge control device (DCD) is configured to limit each discharge current to a fraction of the maximum value of the stimulation current supplied to the associated output (K'i).

21. Control electronics (EC), characterised in that they comprise i) at least one device (ES) according to claim 1, ii) a digital/analogue converter (DAC) capable of converting a current amplitude reference value (Csgn) into a control analogue current (Idac) and coupled to said device (ES) to provide it with said control current (Idac), and iii) a high-voltage supply module (AHT) coupled at least to said anode (A) and configured to polarise said anode (A) under a chosen voltage, so it allows circulation of the currents imposed on each cathode (Ki) via said device (ES).

22. Control electronics according to claim 21, characterised in that said digital/analogue converter (DAC) has what is known as a "unit current source" architecture capable of ensuring the monotonicity of its conversion function.

23. Control electronics according to claim 21, characterised in that said high-voltage supply module (AHT) is a "DC/DC"-type converter.

24. Control electronics according to claim 23, characterised in that said high-voltage supply module (AHT) is an inductive storage chopper.

25. Control electronics according to claim 23, characterised in that said high-voltage supply module (AHT) comprises a capacitive storage charge pump.

26. Control electronics according to claim 25, characterised in that said high-voltage supply module (AHT) further comprises a voltage multiplexer (MUX) coupled to said charge pump.

27. Control electronics according to claim 26, characterised in that said high-voltage supply module (AHT) is configured to operate continuously or discontinuously.

28. Distributed stimulation unit (I, USR) comprising at least one multipolar electrode (EM) comprising at least one anode (A) and at least two cathodes (Ki), characterised in that it further comprises at least one control electronics (EC) according to claim 21.

29. Distributed stimulation unit according to claim 28, characterised in that it comprises a digital controller (CN) capable of supplying said current amplitude reference value (Csgn) and of defining the values of said cutTent fractions (Iki) supplied to said outputs (K'i) of said reconfigurable multi-output current mirror (MC).

30. Distributed stimulation unit according to claim 29, characterised in that said digital controller (CN) and said control electronics (EC) respectively form a digital part and an analogue part of a mixed-type ASIC.

31. Distributed stimulation unit according to claim 28, characterised in that it comprises wave transmission means (MT) and management means configured to manage said data transmission in accordance with a protocol chosen between it and a controller (CR) of a stimulation system (IS).

32. Distributed stimulation unit according to claim 28, characterised in that it comprises wired bus transmission means (MT) and management means configured to manage the data transmission in accordance with a protocol chosen between it and a controller (CR) of a stimulation system (IS).

33. Distributed stimulation unit according to claim 28, characterised in that said digital controller (CN) is configured to deduce, from the values of the imposed stimulation currents, from the output voltage of said high-voltage supply module (AHT) and from the voltage measurements carried out by the voltage monitoring device (DST) at the terminals of the outputs (K'i) of said reconfigurable multi-output current mirror (MC), the impedance (Zi) of each electrode (Ki), so as to control said polarisation of the anode (A).

34. Distributed stimulation unit according to claim 28, characterised in that it forms an implant (I).

35. Stimulation system (IS), characterised in that it comprises at least one distributed stimulation unit (I, USR) according to claim 28 and a controller (CR) configured to exchange data with each distributed stimulation unit (I, USR).

36. Protocol for communication between a controller (CR) of an installation (IS) according to claim 35 and at least one distributed stimulation unit (I, USR), via a medium, characterised in that it consists in managing access to said medium in accordance with a principle of the right to speak of group(s) of distributed stimulation units (I, USR) at sliding intervals, based on an automatic positioning of time intervals which is dependent on levels of priority respectively associated with each node within its group and on topological characteristics.

37. Communication protocol according to claim 36, characterised in that said topological characteristics comprise at least a data rate and a propagation time.

38. Communication protocol according to claim 36, characterised in that said means for managing access to the medium is configured to optimise the exploitation of the bandwidth.

39. Use of the current distribution device (ES), the control electronics (EC), the distributed stimulation unit (I, USR), the stimulation system (IS) and the communication protocol according to claim 36, for the stimulation of animal or human nerve(s) and/or muscle(s).

* * * * *